United States Patent
Kobayashi et al.

(10) Patent No.: US 10,722,105 B2
(45) Date of Patent: Jul. 28, 2020

(54) MEDICAL IMAGING DEVICE, MEDICAL IMAGE ACQUISITION SYSTEM, AND ENDOSCOPE APPARATUS

(71) Applicant: SONY OLYMPUS MEDICAL SOLUTIONS INC., Tokyo (JP)

(72) Inventors: Motoaki Kobayashi, Tokyo (JP); Yuichi Yamada, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 206 days.

(21) Appl. No.: 15/384,765

(22) Filed: Dec. 20, 2016

(65) Prior Publication Data

US 2017/0215711 A1  Aug. 3, 2017

(30) Foreign Application Priority Data

Jan. 29, 2016 (JP) .................. 2016-016430

(51) Int. Cl.
*A61B 1/00* (2006.01)
*H04N 5/225* (2006.01)
(Continued)

(52) U.S. Cl.
CPC .......... *A61B 1/00186* (2013.01); *A61B 1/043* (2013.01); *A61B 1/05* (2013.01);
(Continued)

(58) Field of Classification Search
CPC ....... A61B 1/00186; A61B 1/043; A61B 1/05; A61B 1/0638; G01J 1/00;
(Continued)

(56) References Cited

U.S. PATENT DOCUMENTS

| 2002/0138008 A1* | 9/2002 | Tsujita | A61B 1/00009 600/473 |
|---|---|---|---|
| 2007/0015963 A1* | 1/2007 | Fengler | A61B 1/00009 600/109 |

(Continued)

FOREIGN PATENT DOCUMENTS

| JP | 2001-178672 A | 7/2001 |
|---|---|---|
| JP | 2007-50106 | 3/2007 |

(Continued)

OTHER PUBLICATIONS

Office Action dated Dec. 10, 2019 in Japanese Patent Application No. 2016-016430, 4 pages.

(Continued)

*Primary Examiner* — Mohammed S Rahaman
(74) *Attorney, Agent, or Firm* — Xsensus LLP

(57) ABSTRACT

A medical imaging device includes: a spectroscopic unit that separates light into a first light component of a wavelength band and a second light component; a first imaging element that includes a plurality of first pixels configured to receive the first light component and convert the first light component into electric signals; and a second imaging element that includes a plurality of second pixels and includes a first color filter on which first filters configured to transmit the light component of the wavelength band of one color in the light components of the wavelength bands of two colors that are contained in the second light component and second filters configured to transmit light components of a plurality of wavelength bands including at least the wavelength band of another color in the light components of the wavelength bands of the two colors are arranged.

8 Claims, 11 Drawing Sheets

| $G_{11}$ | $W_{12}$ | $G_{13}$ | $W_{14}$ | ... |
|---|---|---|---|---|
| $W_{21}$ | $W_{22}$ | $W_{23}$ | $W_{24}$ | ... |
| $G_{31}$ | $W_{32}$ | $G_{33}$ | $W_{34}$ | ... |
| $W_{41}$ | $W_{42}$ | $W_{43}$ | $W_{44}$ | ... |
| ⋮ | ⋮ | ⋮ | ⋮ | ⋱ |

(51) Int. Cl.
  *A61B 1/04*   (2006.01)
  *G01J 3/36*   (2006.01)
  *G01J 1/00*   (2006.01)
  *A61B 1/06*   (2006.01)
  *G01J 3/28*   (2006.01)
  *A61B 1/05*   (2006.01)
  *G02B 23/24*  (2006.01)
  *G01J 3/12*   (2006.01)
  *G01J 3/02*   (2006.01)

(52) U.S. Cl.
  CPC .............. *A61B 1/0638* (2013.01); *G01J 1/00* (2013.01); *G01J 3/2803* (2013.01); *G01J 3/36* (2013.01); *G02B 23/2461* (2013.01); *G02B 23/2484* (2013.01); *H04N 5/2256* (2013.01); *H04N 5/2258* (2013.01); *G01J 3/0248* (2013.01); *G01J 2003/1217* (2013.01); *G01J 2003/2806* (2013.01); *H04N 2005/2255* (2013.01)

(58) Field of Classification Search
  CPC ....... G01J 2003/1217; G01J 2003/2806; G01J 3/0248; G01J 3/2803; G01J 3/36; G02B 23/2461; G02B 23/2484; H04N 2005/2255; H04N 5/2256; H04N 5/2258
  See application file for complete search history.

(56) References Cited

U.S. PATENT DOCUMENTS

| 2007/0115376 | A1* | 5/2007 | Igarashi | H04N 9/09 348/262 |
| 2009/0021739 | A1* | 1/2009 | Tsujita | A61B 1/00163 356/407 |
| 2010/0245616 | A1* | 9/2010 | Yoshino | A61B 1/0638 348/223.1 |
| 2013/0100272 | A1* | 4/2013 | Price | G02B 7/38 348/79 |
| 2017/0176336 | A1* | 6/2017 | Dimitriadis | A61B 1/043 |

FOREIGN PATENT DOCUMENTS

| JP | 2007-135951 | 6/2007 |
| JP | 2012-20080 A | 2/2012 |
| JP | 2015-116328 | 6/2015 |

OTHER PUBLICATIONS

Japanese Office Action dated Mar. 31, 2020 in Japanese Application No. 2016-016430.

* cited by examiner

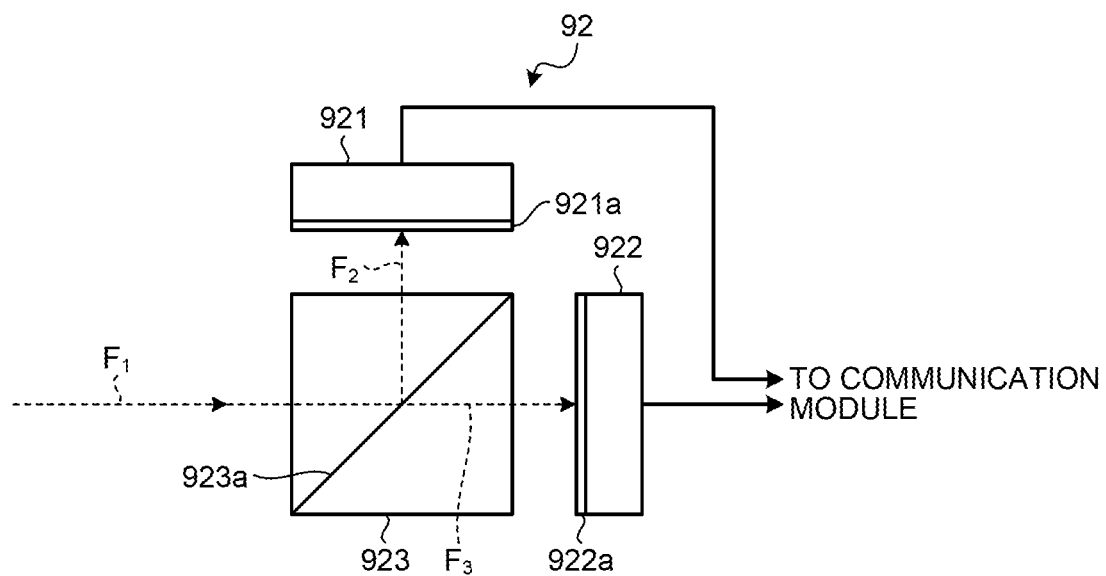

| R₁₁ | W₁₂ | R₁₃ | W₁₄ | ... |
|---|---|---|---|---|
| W₂₁ | W₂₂ | W₂₃ | W₂₄ | ... |
| R₃₁ | W₃₂ | R₃₃ | W₃₄ | ... |
| W₄₁ | W₄₂ | W₄₃ | W₄₄ | ... |
| ⋮ | ⋮ | ⋮ | ⋮ | ⋱ |

| Cy₁₁ | W₁₂ | Cy₁₃ | W₁₄ | ... |
|---|---|---|---|---|
| W₂₁ | W₂₂ | W₂₃ | W₂₄ | ... |
| Cy₃₁ | W₃₂ | Cy₃₃ | W₃₄ | ... |
| W₄₁ | W₄₂ | W₄₃ | W₄₄ | ... |
| ⋮ | ⋮ | ⋮ | ⋮ | ⋱ |

| $G_{11}$ | $G_{12}$ | $G_{13}$ | $G_{14}$ | ⋯ |
|---|---|---|---|---|
| $G_{21}$ | $G_{22}$ | $G_{23}$ | $G_{24}$ | ⋯ |
| $G_{31}$ | $G_{32}$ | $G_{33}$ | $G_{34}$ | ⋯ |
| $G_{41}$ | $G_{42}$ | $G_{43}$ | $G_{44}$ | ⋯ |
| ⋮ | ⋮ | ⋮ | ⋮ | ⋱ |

| $B_{11}$ | $W_{12}$ | $B_{13}$ | $W_{14}$ | ⋯ |
|---|---|---|---|---|
| $W_{21}$ | $W_{22}$ | $W_{23}$ | $W_{24}$ | ⋯ |
| $B_{31}$ | $W_{32}$ | $B_{33}$ | $W_{34}$ | ⋯ |
| $W_{41}$ | $W_{42}$ | $W_{43}$ | $W_{44}$ | ⋯ |
| ⋮ | ⋮ | ⋮ | ⋮ | ⋱ |

MEDICAL IMAGING DEVICE, MEDICAL IMAGE ACQUISITION SYSTEM, AND ENDOSCOPE APPARATUS

CROSS-REFERENCE TO RELATED APPLICATION(S)

The present application claims priority to and incorporates by reference the entire contents of Japanese Patent Application No. 2016-016430 filed in Japan on Jan. 29, 2016.

BACKGROUND

The present disclosure relates to a medical imaging device, a medical image acquisition system, and an endoscope apparatus.

In recent years, observation methods for performing special light observation with special light have been devised separately from normal observation with white light. To be specific, examples of the special light observation include a technique called narrow band imaging (NBI), a technique called infra-red imaging (IRI), a technique called auto fluorescence imaging (AFI), and a technique called photodynamic diagnosis (PDD).

In the NBI, states of blood vessels in a mucous membrane surface layer and a deeper layer are observed using difference in absorption by hemoglobin between narrow band illumination light having a center wavelength of 415 nm and narrow band illumination light having a center wavelength of 540 nm that are emitted thereto. The hemoglobin in the mucous membrane surface layer absorbs the light of 415 nm and the hemoglobin in the deeper layer absorbs the light of 540 nm.

In the IRI, a drug called indocyanine green (ICG) having an absorption peak at near infrared light of a wavelength of around 805 nm in blood is injected intravenously as a contrast agent and near infrared light having a center wavelength of 805 nm and near infrared light having a center wavelength of 940 nm are emitted to observe shadow of blood vessel portions in a mucous membrane lower layer by absorption of the light by the ICG and diagnose running states of blood vessels and lymphatic vessels. In the IRI, the intensity of the light having the center wavelength of 805 nm varies depending on presence and absence of a tumor.

In the AFI, a fluorescent image emitted from a subject is observed by previously administering a fluorescent agent into the subject and irradiating the subject with exciting light. Furthermore, a tumor portion is diagnosed by observing presence and absence of the fluorescent image and a shape thereof. Fluorescence from the fluorescent agent is emitted in the mucous membrane surface layer in a normal tissue whereas fluorescence from the fluorescent agent is significantly lowered when an accumulation of blood vessels or mucous membrane thickening due to lesions occurs in the mucous membrane surface layer.

In the PDD, an image on which cancer cells and normal cells are easy to be distinguished from each other is provided using the following characteristics. That is, when a solution of aminolevulinic acid (5-ALA) is dosed to a patient, it is metabolized by a blood material (heme) in a normal tissue in the body but it is not metabolized and is accumulated as a material called PpIX as an intermediate product thereof in the cancer cells. When the PpIX is irradiated with blue light (center wavelength of 410 nm), the PpIX emits fluorescence of red (peak wavelength of 630 nm). It should be noted that the normal cells emit blue light on reception of the irradiated blue light, for example, light of 460 nm on the bottom of the irradiated blue light.

As endoscope apparatuses capable of performing the special light observation, a dedicated endoscope apparatus and an endoscope apparatus using another imaging element for special light have been known. The dedicated endoscope apparatus, however, has a problem in that endoscopes for the normal observation and the special light observation need to be switched during surgery. On the other hand, the endoscope using another imaging element for the special light does not use pixel information of the imaging element for the special light in the normal observation and does not use pixel information of an imaging element for normal light in the special light observation. That is to say, the endoscope apparatus uses only one of the two imaging elements and the configuration thereof is not effective.

In the special light observation, in the NBI, imaging is performed using pixels receiving a light component of a wavelength band of blue (hereinafter, also referred to as B pixels) and pixels receiving a light component of a wavelength band of green (hereinafter, also referred to as G pixels). When a usual single-plate-type imaging element of the Bayer array is used, imaging is performed while the number of G pixels is half of the total number of pixels and the number of B pixels is quarter thereof, resulting in generation of an image deteriorated in resolution relative to the normal light.

In the IRI, a usual single-plate-type imaging element of the Bayer array performs imaging using infrared-sensitive regions of pixels receiving a light component of a wavelength band of red (hereinafter, also referred to as R pixels), the G pixels, and the B pixels. In this case, the B pixels have regions in which light receiving sensitivity to the wavelength band of infrared rays is low and the quarter of an acquired image is generated based on information provided by the low-sensitivity imaging, resulting in lowering of sensitivity.

In the AFI, a barrier filter for cutting light of a wavelength of equal to or lower than 500 nm needs to be provided on a light path of an imaging optical system and needs to be inserted or removed for switching between the AFI and the normal observation. When the insertion and removal of the barrier filter is difficult in terms of a space, a dedicated optical system and a dedicated imaging system need to be separately provided, resulting in size increase of the apparatus configuration. This causes a problem in that there is no choice but to employ a small-sized imaging element having the small number of pixels for the space.

In the PDD, imaging is performed using the R pixels and the B pixels. When the usual single-plate-type imaging element of the Bayer array is used, imaging is performed with the quarter of the total number of pixels for each of the R pixels and the B pixels, resulting in generation of an image deteriorated in resolution for the normal light.

For example, Japanese Patent Application Laid-open No. 2007-135951 discloses, as a single-plate-type imaging element, an imaging element in which the B pixels and pixels receiving a light component of a wavelength band of white (hereinafter, also referred to as W pixels), pixels receiving a light component of a wavelength band of cyan (hereinafter, also referred to as Cy pixels), or pixels receiving a light component of a wavelength band of magenta (hereinafter, also referred to as Mg pixels) are arranged, and the number of pixels receiving the light component of the wavelength band of green is equal to or more than the half of the total number of pixels and the number of pixels receiving the light component of the wavelength band of blue is equal to or more than the half of the number of pixels receiving the light component of the wavelength band of green.

In order to provide a finer observation image, imaging devices receiving observation light using a plurality of imaging elements have been known (for example, see Japanese Patent Application Laid-open No. 2015-116328). The imaging device as disclosed in Japanese Patent Application Laid-open No. 2015-116328 has the configuration in which a dichroic mirror reflecting a light component of the wavelength band of green and transmitting light components of the wavelength bands of red and blue, an imaging element receiving the light component reflected by the dichroic mirror, a filter transmitting the light component of the wavelength band of red, and a filter transmitting the light component of the wavelength band of blue are aligned, and imaging elements receiving the light components that have passed through the filters among the light components that have passed through the dichroic mirror are used to generate an image based on electric signals generated by the respective imaging elements.

SUMMARY

The technique disclosed in Japanese Patent Application Laid-open No. 2007-135951 does not, however, take special light observation other than the NBI into consideration although a high-quality image may be provided in the normal observation and the NBI. The technique disclosed in Japanese Patent Application Laid-open No. 2015-116328 does not take the special light observation into consideration and may not be applied to the above-mentioned various special light observations.

The configuration of an imaging device including three-plate-type imaging elements instead of the single-plate-type or double-plate-type imaging element(s) may be considered. The three-plate-type imaging elements have an advantage that color reproducibility is enhanced because color separation into all colors of the R pixels, the G pixels, and the B pixels is performed and the imaging elements for the respective colors provide images but has a problem of increase in size and weight due to the three-plate type. In addition, in order to provide fixing accuracy for making optical relative positions of the three imaging elements coincide with one another, a precise and advanced adjustment technique and an expensive adjustment device are required and the degree of difficulty in manufacturing is increased, resulting in problems of difficulty in ensuring quality and increase in manufacturing cost.

There is a need for a medical imaging device, a medical image acquisition system, and an endoscope apparatus which acquires an observation image with high quality while preventing increase in size and weight.

According to one aspect of the present disclosure, there is provided a medical imaging device including: a spectroscopic unit that separates light from an outside into a first light component of a wavelength band of any one color among wavelength bands of red, green, and blue and a second light component containing light components of wavelength bands of two colors that differ from the wavelength band of the first light component; a first imaging element that includes a plurality of first pixels configured to receive the first light component separated by the spectroscopic unit and convert the first light component into electric signals; and a second imaging element that includes a plurality of second pixels arranged with a same arrangement and interval as the first pixels in the first imaging element, and includes a first color filter on which first filters configured to transmit the light component of the wavelength band of one color in the light components of the wavelength bands of the two colors that are contained in the second light component and second filters configured to transmit light components of a plurality of wavelength bands including at least the wavelength band of another color in the light components of the wavelength bands of the two colors are arranged at sides of light receiving surfaces of the second pixels in accordance with the arrangement of the second pixels.

BRIEF DESCRIPTION OF THE DRAWINGS

FIG. 3 is a schematic plan view for explaining the configuration of an imaging unit in the first embodiment of the present disclosure;

FIG. 4 is a schematic plan view for explaining the configuration of pixels of an imaging element of the imaging unit in the first embodiment of the present disclosure;

FIG. 8 is a view for explaining a pixel array of an imaging element according to a first modification of the first embodiment of the present disclosure;

FIG. 9 is a view for explaining a pixel array of an imaging element according to a second modification of the first embodiment of the present disclosure;

FIG. 11 is a view for explaining a pixel array of an imaging element according to a third modification of the first embodiment of the present disclosure;

FIG. 12 is a view for explaining a pixel array of an imaging element in the third modification of the first embodiment of the present disclosure;

DETAILED DESCRIPTION

Figure 1:
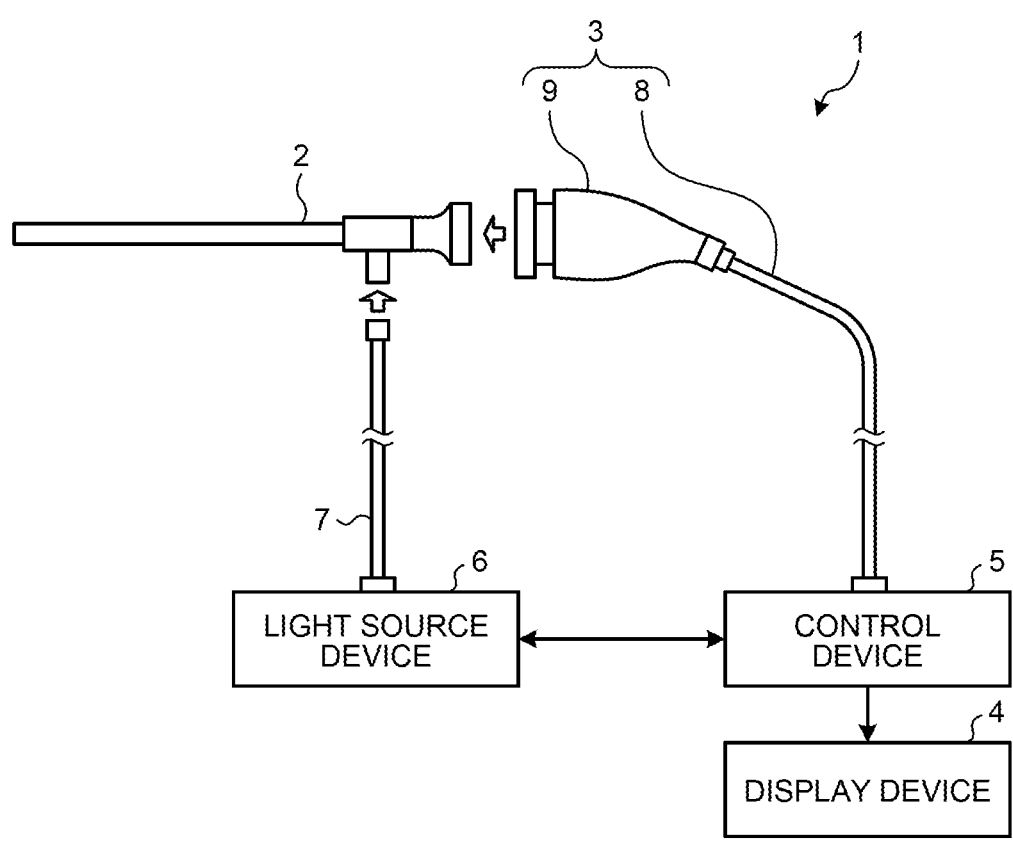
FIG. 1 is a view illustrating the schematic configuration of an endoscope apparatus according to a first embodiment of the present disclosure.

Hereinafter, modes for carrying out the present disclosure (hereinafter, referred to as "embodiments") will be described. In the embodiments, as an example of a medical image acquisition system including a medical imaging device according to the present disclosure, a medical endoscope apparatus imaging and displaying an image of the interior of a subject such as a patient will be described. Furthermore, the embodiments do not limit the present disclosure. The same reference numerals denote the same portions in illustration of the drawings.

First Embodiment

FIG. 1 is a view illustrating the schematic configuration of an endoscope apparatus 1 according to a first embodiment of the present disclosure. The endoscope apparatus 1 is used in a medical field and is an apparatus for observing an object in the interior (in a living body) of an observation target such as a human. As illustrated in FIG. 1, the endoscope apparatus 1 includes an endoscope 2, an imaging device 3 (medical imaging device), a display device 4, a control device 5 (image processing device), and a light source device 6, and the imaging device 3 and the control device 5 configure a medical image acquisition system. In the first embodiment, the endoscope 2 and the imaging device 3 configure an endoscope apparatus using a rigid scope.

The light source device 6 supplies white illumination light for illuminating the interior of the living body to one end of a light guide 7 while the one end of the light guide 7 is connected to the endoscope 2. The one end of the light guide 7 is connected to the light source device 6 in a detachable manner and the other end thereof is connected to the endoscope 2 in a detachable manner. The light guide 7 transmits the light supplied from the light source device 6 to the other end from the one end to supply the light to the endoscope 2.

The imaging device 3 images an object image from the endoscope 2 and outputs an imaged result. As illustrated in FIG. 1, the imaging device 3 includes a transmission cable 8 as a signal transmitter and a camera head 9. In the first embodiment, the transmission cable 8 and the camera head 9 configure the medical imaging device.

The endoscope 2 is rigid, has an elongated shape, and is inserted into the living body. The endoscope 2 includes an optical system that is configured using one or a plurality of lenses and collects the object image. The endoscope 2 outputs the light supplied through the light guide 7 from the leading end thereof and irradiates the interior of the living body with the light. The optical system (lens unit 91) in the endoscope 2 collects the light (object image) with which the interior of the living body has been irradiated.

The camera head 9 is connected to a base end of the endoscope 2 in a detachable manner. The camera head 9 images the object image collected by the endoscope 2 and outputs imaging signals by the imaging under control by the control device 5. It should be noted that the detail configuration of the camera head 9 will be described later.

One end of the transmission cable 8 is connected to the control device 5 through a connector in a detachable manner and the other end thereof is connected to the camera head 9 through a connector in a detachable manner. To be specific, the transmission cable 8 is a cable in which a plurality of electric wirings (not illustrated) are arranged at the inner side of an outer coating as an outermost layer. The electric wirings are used for transmitting the imaging signals that are output from the camera head 9, and a control signal, a synchronization signal, a clock, and electric power that are output from the control device 5 to the camera head 9.

The display device 4 displays an image generated by the control device 5 under control by the control device 5. Although the display device 4 preferably includes a display unit of equal to or larger than 55 inches in order to provide immersion feeling in observation, the display device 4 is not limited to include the display unit of the above-mentioned size.

The control device 5 processes the imaging signals input from the camera head 9 through the transmission cable 8, outputs an image signal to the display device 4, and collectively controls operations of the camera head 9 and the display device 4. It should be noted that the detail configuration of the control device 5 will be described later.

Figure 2:
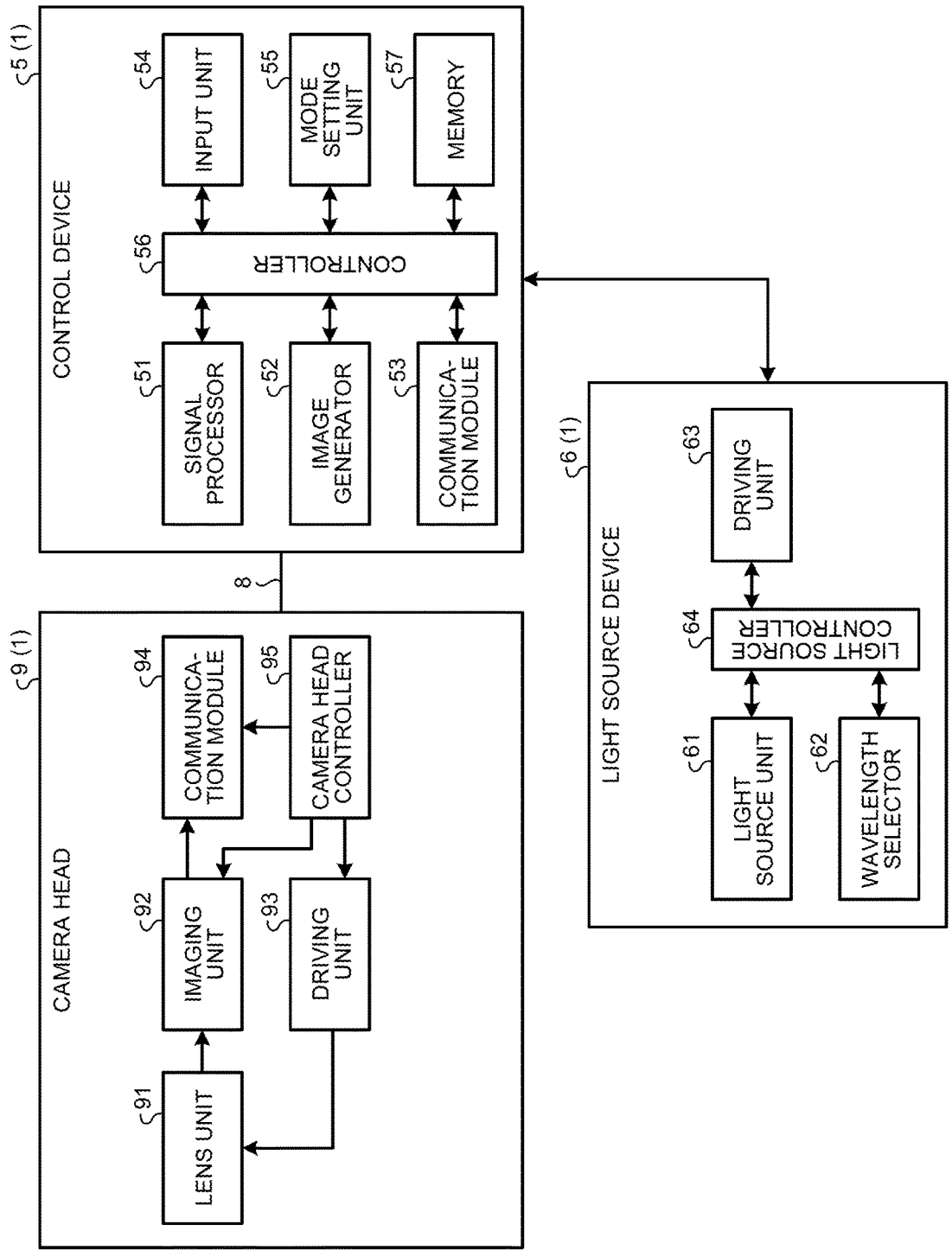
FIG. 2 is a block diagram illustrating the configurations of a camera head, a control device, and a light source device illustrated in FIG. 1.

Next, the configurations of the camera head 9, the control device 5, and the light source device 6 will be described. FIG. 2 is a block diagram illustrating the configurations of the camera head 9, the control device 5, and the light source device 6. In FIG. 2, the connectors enabling the camera head 9 and the transmission cable 8 to be detachably attached are not illustrated.

Hereinafter, the configuration of the control device 5, the configuration of the light source device 6, and the configuration of the camera head 9 are described in this order. The following mainly describes a main part of the present disclosure as the configuration of the control device 5. As illustrated in FIG. 2, the control device 5 includes a signal processor 51, an image generator 52, a communication module 53, an input unit 54, a mode setting unit 55, a controller 56, and a memory 57. The control device 5 may include a power supply unit (not illustrated) that generates a power supply voltage for driving each of the control device 5, the camera head 9, and the light source device 6, supplies it to the respective units of the control device 5, and supplies it to the camera head 9 through the transmission cable 8, and the like.

The signal processor 51 performs signal processing such as noise removal and, if necessary, A/D conversion on the imaging signals output from the camera head 9 and outputs the digitized imaging signals (pulse signals) to the image generator 52.

The signal processor 51 generates synchronization signals and clocks of the imaging device 3, the control device 5, and the light source device 6. The synchronization signal (for example, a synchronization signal instructing an imaging timing of the camera head 9) and the clock (for example, a clock for serial communication) to the imaging device 3 are transmitted to the imaging device 3 through a line (not illustrated) and the imaging device 3 is driven based on the synchronization signal and the clock.

The image generator 52 generates an image signal for display that the display device 4 displays based on the imaging signals input from the signal processor 51. The image generator 52 executes predetermined signal processing on the imaging signals to generate the image signal for display that includes the object image. Examples of the image processing include various pieces of image processing such as interpolation processing, color correction processing, color emphasizing processing, and contour emphasizing processing. The image generator 52 outputs the generated image signal to the display device 4.

The communication module 53 outputs signals from the control device 5 that include a control signal, which will be described later, transmitted from the controller 56 to the imaging device 3. Furthermore, the communication module 53 outputs the signals from the imaging device 3 to the control device 5. That is to say, the communication module 53 is a relay device that collectively outputs signals from the respective units of the control device 5 to be output to the imaging device 3 by, for example, parallel-to-serial conversion, and distributes the signals input from the imaging device 3 by, for example, serial-to-parallel conversion and outputs the distributed signals to the respective units of the control device 5.

The input unit 54 is implemented using a user interface such as a keyboard, a mouse, and a touch panel and receives input of various pieces of information.

The mode setting unit 55 performs setting of an observation mode based on observation method setting information received by the input unit 54.

The controller 56 controls driving of the respective components including the control device 5, the camera head 9, and the light source device 6, controls input and output of pieces of information to the respective components, and so on. The controller 56 generates the control signal with reference to communication information data (for example, communication format information) recorded in the memory 57 and transmits the generated control signal to the imaging device 3 through the communication module 53. The controller 56 outputs the control signal to the camera head 9 through the transmission cable 8.

The memory 57 is implemented using a semiconductor memory such as a flash memory and a dynamic random access memory (DRAM), and records therein the communication information data (for example, communication format information). The memory 57 may record therein various types of programs that the controller 56 executes, and the like.

The signal processor 51 may include an AF processor that outputs predetermined AF evaluation values of respective frames based on input imaging signals of the frames and an AF operation unit that performs AF operation processing of selecting a frame, a focus lens position, or the like optimum as a focusing position based on the AF evaluation values of the respective frames from the AF processor.

Each of the above-mentioned signal processor 51, image generator 52, communication module 53, and controller 56 is implemented using a general processor such as a central processing unit (CPU) with an internal memory (not illustrated) recording therein programs or a dedicated processor like various types of operation circuits executing specific functions, such as an application specific integrated circuit (ASIC). Alternatively, each of them may be configured using a field programmable gate array (FPGA) (not illustrated) as one type of programmable integrated circuits. When each of them is configured by the FPGA, the FPGA as the programmable integrated circuit may be configured by configuration data read from a memory while the memory storing therein the configuration data is provided.

Next, the main part of the present disclosure will be described as the configuration of the light source device 6. As illustrated in FIG. 2, the light source device 6 includes a light source unit 61, a wavelength selector 62, a driving unit 63, and a light source controller 64.

The light source unit 61 outputs white light containing light components of wavelength bands of red, green, and blue under control by the light source controller 64. The white light generated by the light source unit 61 is output to the light guide 7 through the wavelength selector 62. The light source unit 61 is implemented using a light source emitting white light, such as a light emitting diode (LED), a xenon lamp, and a laser.

The wavelength selector 62 selects a wavelength band in the white light output from the light source unit 61 in accordance with the observation mode set by the mode setting unit 55 and causes a light component of the selected wavelength band to be incident on the light guide 7. The wavelength selector 62 is implemented using, for example, a rotating filter on which a plurality of filters capable of being arranged on a light path of the white light that is output from the light source unit 61 are provided. The wavelength selector 62 may change the wavelength band of the light component to be made incident on the light guide by rotating the rotating filter to switch the filter that is arranged on the light path under control by the light source controller 64.

The driving unit 63 is configured using a motor or the like, and rotationally drives the rotating filter of the wavelength selector 62, for example.

The light source controller 64 controls the light source unit 61 to turn ON/OFF the output of the white light, and controls the type (wavelength band) of the illumination light to be output from the light source device 6 by controlling the driving unit 63 to rotate the rotating filter such that any filter thereof is arranged on the light path of the light source unit 61.

Table 1 indicates wavelength bands of the illumination light in accordance with the respective observation methods. To be specific, in the normal observation, a light component of a wavelength band Wb of 400 nm to 700 nm is output. In the NBI, narrow band light components of a wavelength band Bn (390 nm to 445 nm) having a center wavelength of 415 nm and a wavelength band Gn (530 nm to 550 nm) having a center wavelength of 540 nm are output. In the IRI, near infrared light components of a wavelength band IR-1 (790 nm to 820 nm) having a center wavelength of 805 nm and a wavelength band IR-2 (905 nm to 970 nm) having a center wavelength of 940 nm are output. In the AFI, light components of a wavelength band Ba of 390 nm to 470 nm and a wavelength band Ga-1 of 540 nm to 560 nm are output. In the PDD, a narrow band light component of a wavelength band Bp including wavelengths around a center wavelength of 410 nm is output. In the normal observation, a filter for cutting the infrared light component is arranged on the light source device 6 or the camera head 9. In the NBI, the AFI, and the PDD, the infrared light component may be cut or may be made incident on the light guide 7. In the IRI, the infrared light component is made incident on the light guide 7 without being cut.

TABLE 1

| OBSERVATION METHOD | ILLUMINATION LIGHT | | | FACE SEQUENTIAL METHOD/ SIMULTANEOUS METHOD | RECEPTION LIGHT | |
|---|---|---|---|---|---|---|
| | BAND NAME | WAVELENGTH [nm] | NECESSITY OF IR CUT | | BAND NAME | WAVELENGTH [nm] |
| NORMAL | Wb | 400 TO 700 | NECESSARY | BOTH AVAILABLE | Wb | 400 TO 700 |

TABLE 1-continued

| OBSERVATION METHOD | ILLUMINATION LIGHT | | | FACE SEQUENTIAL METHOD/ SIMULTANEOUS METHOD | RECEPTION LIGHT | |
|---|---|---|---|---|---|---|
| | BAND NAME | WAVELENGTH [nm] | NECESSITY OF IR CUT | | BAND NAME | WAVELENGTH [nm] |
| NBI | Bn | 415 (390 TO 445) | — | BOTH AVAILABLE | Bn | 415 (390 TO 445) |
| | Gn | 540 (530 TO 550) | | | Gn | 540 (530 TO 550) |
| IR-1 | IR-1 | 805 (790 TO 820) | UNNECESSARY | FACE SEQUENTIAL METHOD | IR-1 | 805 (790 TO 820) |
| | IR-2 | 940 (905 TO 970) | | | IR-2 | 940 (905 TO 970) |
| AFI | Ga-1 | 540 TO 560 | — | FACE SEQUENTIAL METHOD | Ga-1 | 540 TO 560 |
| | Ba | 390 TO 470 | | | Ga-2 | 500 TO 630 |
| PDD | Bp | AROUND 410 | — | BOTH AVAILABLE | Bp-1 | 460 AND HIGHER |
| | | | | | Rp | AROUND 630 |

As indicated in Table 1, in the normal observation, the NBI, and the PDD, a light reception method of the illumination light may be a face sequential method or a simultaneous method. In the IRI and the AFI, the light reception method of the illumination light is the face sequential method. The simultaneous method is a method in which light components of a plurality of colors configuring an image are simultaneously received. On the other hand, the face sequential method is a method in which the light components of the colors configuring the image are separately received. Hereinafter, in the embodiment, it is assumed that the camera head 9 receives the light components by the simultaneous method in the normal observation, the NBI, and the PDD and receives the light components by the face sequential method in the IRI and the AFI.

As indicated in Table 1, in the normal observation, the endoscope 2 receives the light component of the wavelength band Wb. In the NBI, the endoscope 2 receives the narrow band light components of the wavelength band Bn and the wavelength band Gn. In the IRI, the endoscope 2 receives the near infrared light components of the wavelength band IR-1 and the wavelength band IR-2. In the AFI, the endoscope 2 receives the light component of the wavelength band Ga-1 of 540 nm to 560 nm that has been reflected from the object and a light component of a wavelength band Ga-2 of 500 nm to 630 nm that includes a light component reflected from the object and auto fluorescence emitted by excitation of the object. In the PDD, the endoscope 2 receives a light component of a wavelength band Bp-1 of equal to or higher than 460 nm in the case of a normal tissue and a light component of a wavelength band Rp of around 630 nm in the case of cancer cells, they being fluorescence emitted by a tissue excited by the light component of the wavelength band Bp. In the AFI, the endoscope 2 also receives the light component of the wavelength band Ba of 390 nm to 470 nm that is used as the exciting light but does not handle it as a received light component because it is not used for image generation.

The light source device 6 may have the configuration in which the light source unit 61 has a plurality of light sources each of which outputs light of a wavelength band in accordance with each observation method without providing the rotating filter instead of the configuration in which the rotating filter of the wavelength selector 62 changes the wavelength band of the light component to be output. The light sources are implemented using, for example, a plurality of LEDs having different light wavelength bands to be output.

Next, the main part of the present disclosure will be described as the configuration of the camera head 9. As illustrated in FIG. 2, the camera head 9 includes the lens unit 91, an imaging unit 92, a driving unit 93, a communication module 94, and a camera head controller 95.

The lens unit 91 is configured using one or a plurality of lenses and forms the object image collected by the endoscope 2 on imaging surfaces of imaging elements configuring the imaging unit 92. The lens(es) is(are) configured to be movable along a light axis. The lens unit 91 is provided with an optical zoom mechanism (not illustrated) changing an angle of view and a focus mechanism changing a focal point by moving the lens(es). The lens unit 91 may be provided with, in addition to the optical zoom mechanism and the focus mechanism, a diaphragm mechanism and/or an optical filter (for example, a filter for cutting the infrared light component) capable of being freely inserted on the light axis.

The imaging unit 92 images the object under control by the camera head controller 95. The imaging unit 92 is configured using two imaging elements such as charged coupled devices (CCDs) or complementary metal oxide semiconductors (CMOSs) that receive the object image formed by the lens unit 91 and convert them into electric signals and a prism that separates observation light and causes the separated light components to be incident on the two imaging elements. When the CCDs are employed, for example, a signal processor (not illustrated) that performs signal processing (A/D conversion and the like) on the electric signals (analog signals) from the imaging elements and outputs imaging signals is mounted on a sensor chip or the like. When the CMOSs are employed, for example, the imaging elements include signal processors that perform signal processing (A/D conversion and the like) on the electric signals (analog signals) converted from light and output imaging signals. The configuration of the imaging unit 92 will be described.

FIG. 3 is a schematic plan view for explaining the configuration of the imaging unit 92. As illustrated in FIG. 3, the imaging unit 92 includes a first imaging element 921, a second imaging element 922, and a prism 923. In the imaging unit 92, external observation light is incident on the prism 923 through the lens unit 91 and light components separated by the prism 923 are incident on the first imaging element 921 and the second imaging element 922.

FIG. 4 is a schematic plan view illustrating the configuration of pixels of the imaging element. Although the following describes the pixel configuration of the first imaging element 921 with reference to FIG. 4, the same configuration is applied to the second imaging element 922 and a pixel array of the second imaging element 922 has the same array and interval as those of the pixel array of the first imaging element 921. In the first imaging element 921, a plurality of pixels receiving light from the lens unit 91 and the prism 923 are squarely arrayed two dimensionally (arrayed in a matrix form). The first imaging element 921 performs photoelectric conversion on the light components received by the respective pixels to generate the electric signals (also referred to as image signals or the like). The electric signals include pixel values (luminance values) and pixel positional information of the respective pixels. In FIG. 4, a pixel arranged on an $x^{th}$ row and a $y^{th}$ column is expressed as a pixel $P_{xy}$ (x and y are natural numbers).

The first imaging element 921 and the second imaging element 922 are arranged at positions such that the light receiving surfaces on which the respective pixels receive light are conjugate to a focal plane of the lens unit 91. The position of the pixel $P_{xy}$ on the first imaging element 921 and the position of the pixel $P_{xy}$ on the second imaging element 922 for the light axis of the observation light are identical to each other in the row direction and the column direction. When, for example, the first imaging element 921 and the second imaging element 922 are superimposed on each other while the light axes of the observation light are made uniform, a position of a pixel $P_{11}$ on the first imaging element 921 and a position of a pixel $P_{11}$ on the second imaging element 922 are overlapped with each other. Each of the first imaging element 921 and the second imaging element 922 is fixed by a fixing member (not illustrated) in a state where the light axis direction of the observation light, the yaw direction, the roll direction, the pitch direction, and the two axial directions (the horizontal direction and the perpendicular direction) orthogonal to a plane perpendicular to the light axes are adjusted.

The first imaging element 921 and the second imaging element 922 have a first color filter 921a and a second color filter 922a that are provided on the light receiving surfaces thereof, respectively. The first color filter 921a and the second color filter 922a have a plurality of filters each transmitting a light component of an individually set wavelength band. The first color filter 921a and the second color filter 922a may be provided so as to be bonded to the light receiving surfaces of the first imaging element 921 and the second imaging element 922, respectively, or may be integrally provided on the first imaging element 921 and the second imaging element 922, respectively. The first color filter 921a and the second color filter 922a may be configured such that the filters are integrally provided or the individual filters are provided on the respective light receiving surfaces.

The first color filter 921a and the second color filter 922a are configured such that the filters configured to transmit light components of predetermined wavelength bands are arranged in a matrix form in accordance with arrangement of the pixels $P_{xy}$. In other words, one filter configured to transmit the light component of the predetermined wavelength band is arranged on the light receiving surface of each pixel. The pixel $P_{xy}$ on which the filter is provided therefore receives the light component of the wavelength band that the filter transmits. For example, the pixel $P_{xy}$ on which the filter configured to transmit a light component of a wavelength band of blue is provided receives the light component of the wavelength band of blue. Hereinafter, the pixel $P_{xy}$ that receives the light component of the wavelength band of blue is also referred to as a B pixel in some cases. In the same manner, a pixel that receives a light component of a wavelength band of green is also referred to as a G pixel and a pixel that receives a light component of a wavelength band of red is also referred to as an R pixel in some cases. As the wavelength bands of blue, green, and red, for example, the wavelength band of blue is 380 nm to 500 nm, the wavelength band of green is 480 nm to 600 nm, and the wavelength band of red is 580 nm to 650 nm.

Figure 5:
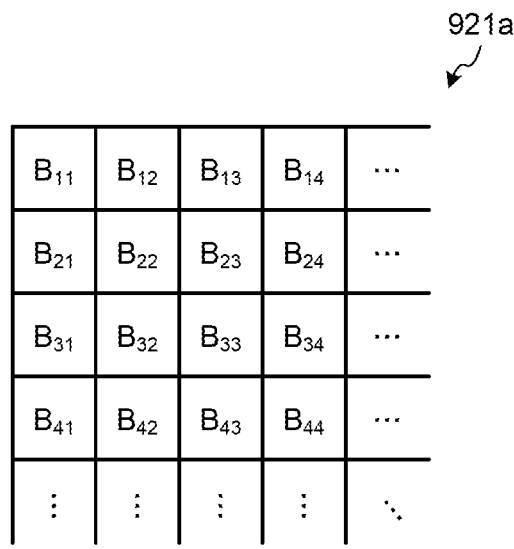
FIG. 5 is a schematic plan view for explaining the configuration of a color filter of the imaging unit in the first embodiment of the present disclosure.

FIG. 5 is a schematic plan view for explaining the configuration of the first color filter of the imaging unit in the first embodiment of the present disclosure and is a schematic plan view illustrating an example of the configuration of the first color filter 921a provided on the first imaging element 921. The first color filter 921a is configured by arranging B filters configured to transmit the light component of the wavelength band of blue in a matrix form in accordance with arrangement of the pixels $P_{xy}$. On the first imaging element 921, the respective pixels $P_{xy}$ therefore receive the light component of the wavelength band of blue that has passed through the first color filter 921a.

Figure 6:
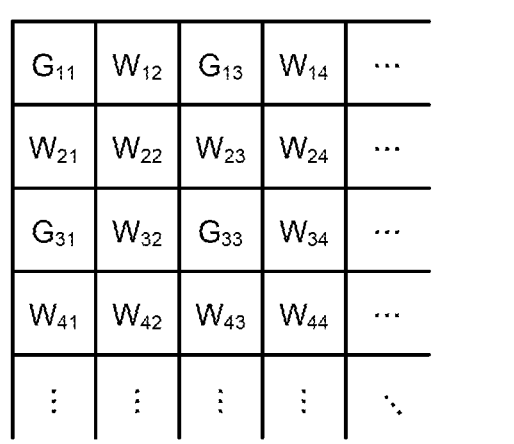
FIG. 6 is a schematic plan view for explaining the configuration of the color filter of the imaging unit in the first embodiment of the present disclosure.

FIG. 6 is a schematic plan view for explaining the configuration of the second color filter of the imaging unit in the first embodiment of the present disclosure, and is a schematic plan view illustrating an example of the configuration of the second color filter 922a provided on the second imaging element 922. The second color filter 922a is configured by arranging G filters configured to transmit the light component of the wavelength band of green and W filters configured to transmit the light component of the wavelength band of white in a matrix form in accordance with arrangement of the pixels $P_{xy}$. On the second color filter 922a, the G filters are arranged every other pixel in the row direction and the column direction and the W filters are arranged at positions at which the G filters are not arranged. On the second imaging element 922, the respective pixels $P_{xy}$ therefore receive the light component of the wavelength band of green or the light components of the wavelength bands of green and red that has(have) passed through the second color filter 922a.

Figure 7:
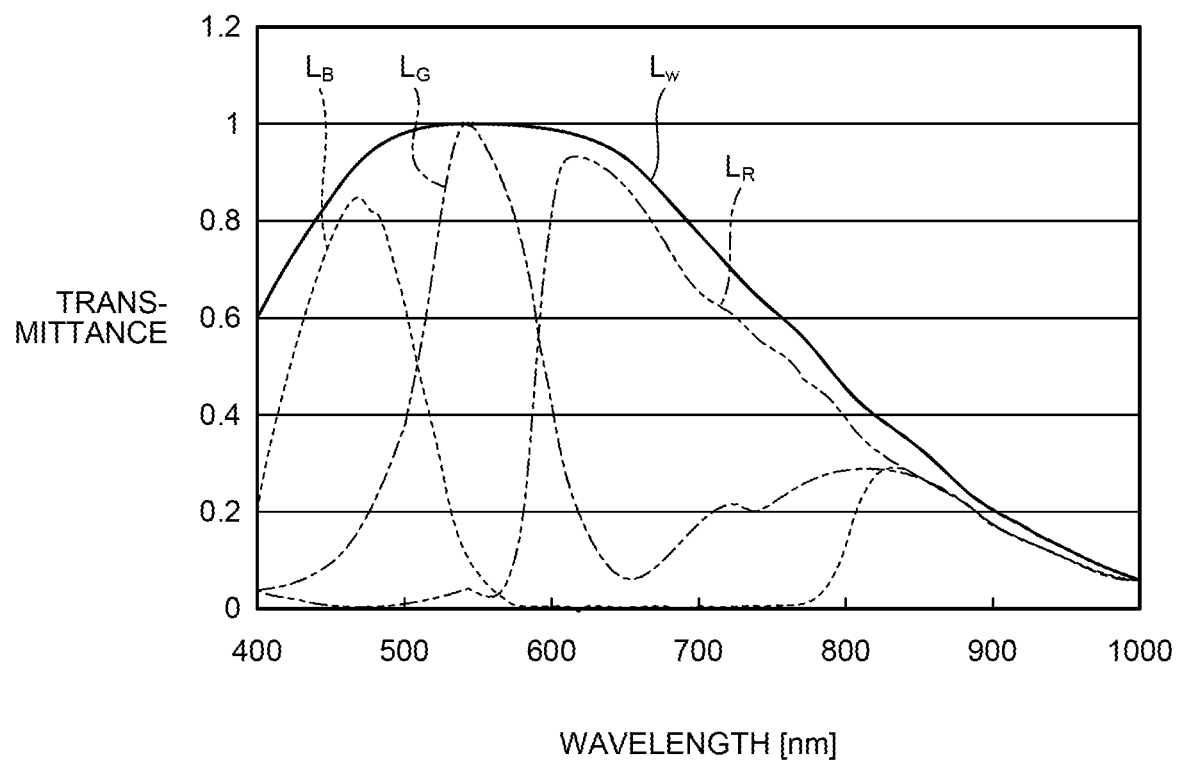
FIG. 7 is a view for explaining wavelength bands of light components that respective filters of the color filter transmit in the first embodiment of the present disclosure.

FIG. 7 is a view for explaining wavelength bands of the light components that respective filters of the color filters transmit in the first embodiment of the present disclosure. In FIG. 7, a transmission curve of an R filter configured to transmit the light component of the wavelength band of red as another primary color filter is also illustrated in addition to transmission curves of the G filter, the B filter, and the W filter. In FIG. 7, a curve $L_R$ indicates the transmission curve of the light component passing through the R filter, a curve $L_G$ indicates the transmission curve of the light component passing through the G filter, a curve $L_B$ indicates the transmission curve of the light component passing through the B filter, and a curve $L_W$ indicates the transmission curve of the light component passing through the W filter. As illustrated in FIG. 7, the respective filters in the first embodiment have sensitivity to the wavelength band of the near infrared rays. To be specific, the W filters have sensitivity to at least 400 nm to 1000 m. The R filters have sensitivity to approximately 580 nm to 1000 m. The G filters have sensitivity to approximately 480 nm to 600 nm and 680 nm to 1000 nm.

The B filters have sensitivity to approximately 380 nm to 500 nm and 800 nm to 1000 nm.

The prism 923 forms a cubic shape by bonding two prisms having triangular columnar shapes and a thin dichroic film 923a is provided between the bonded surfaces of the two prisms. The dichroic film 923a reflects the light component of the wavelength band (for example, 380 nm to 480 nm) of blue and transmits a second light component including the wavelength bands (for example, 480 nm to 650 nm) of red and green and the wavelength band of the near infrared rays. Observation light $F_1$ incident on the prism 923 is therefore separated into a first light component $F_2$ including the wavelength band of blue and a second light component $F_3$ including the wavelength bands of red and green and the wavelength band of the near infrared rays and the separated light components (the first light component $F_2$ and the second light component $F_3$) are output to the outside from the different outer surfaces (planes) of the prism 923 (see FIG. 3). The prism 923 separates the observation light $F_1$ into the first light component $F_2$ and the second light component $F_3$ by reflection and transmission once for each. In the first embodiment, the first light component $F_2$ including the wavelength band of blue is incident on the first imaging element 921 (first color filter 921a) and the second light component $F_3$ including the wavelength bands of red and green are incident on the second imaging element 922 (second color filter 922a). The prism 923 may form a rectangular parallelepiped shape or a polygonal shape instead of the cubic shape as long as it may separate the incident light and output the separated light components.

Table 2 indicates the light wavelength bands that the first imaging element 921 and the second imaging element 922 acquire by the respective observation methods. To be specific, as indicated in Table 2, in the normal observation, the first imaging element 921 receives the light component of the wavelength band Bb of blue on the B pixels. The second imaging element 922 receives the light component of the wavelength band Gb of green on the G pixels and receives the light components of the wavelength band Gb of green and the wavelength band Rb of red on the W pixels.

TABLE 2

| OBSERVATION METHOD | BAND | | | |
|---|---|---|---|---|
| | FIRST IMAGING ELEMENT | | SECOND IMAGING ELEMENT | |
| | PIXEL | ELEMENT | PIXEL | ELEMENT |
| NORMAL | B | Bb | G | Gb |
| | | | W | Gb    Rb |
| NBI | B | Bn | G | Gn |
| | | | W | Gn |
| IRI | B | — | G | (IR-1)    IR-2 |
| | | | W | IR-1    IR-2 |
| AFI | B | — | G | Ga-1    (Ga-2) |
| | | | W | Ga-1    Ga-2 |
| PDD | B | Bp | G | — |
| | | | W | Rp |

In the NBI, the first imaging element 921 receives the light component of the wavelength band Bn on the B pixels. The second imaging element 922 receives the light component of the wavelength band Gn on the G pixels and the W pixels.

In the IRI, the first imaging element 921 does not receive light. The second imaging element 922 receives the light component of the wavelength band IR-2 on the G pixels and receives the light components of the wavelength band IR-1 and the wavelength band IR-2 on the W pixels. The G pixels also receive the light component of the wavelength band IR-1 although sensitivity thereto is low. The G pixels and the W pixels separately receive the light component of the wavelength band IR-1 and the light component of the wavelength band IR-2 with illumination by the face sequential method.

In the AFI, the first imaging element 921 receives the light component of the wavelength band Ba on the B pixels but does not acquire signals thereof because it is not used for image generation. The second imaging element 922 receives the light component of the wavelength band Ga-1 on the G pixels and receives the light components of the wavelength band Ga-1 and the wavelength band Ga-2 on the W pixels. The G pixels also receive the light component of the wavelength band Ga-2 although sensitivity thereto is low. The G pixels and the W pixels separately receive the light component of the wavelength band Ga-1 and the light component of the wavelength band Ga-2 with illumination by the face sequential method. In this case, the dichroic film 923a functions as a barrier filter for preventing the light component of the wavelength band Ba as exciting light from being incident on the second imaging element 922.

In the PDD, the first imaging element 921 receives the light component of the wavelength band Bp on the B pixels. The second imaging element 922 does not receive light on the G pixels and receives the light component of the wavelength band Rp on the W pixels.

The driving unit 93 has a driver operating the optical zoom mechanism and the focus mechanism to change the angle of view and the focal point position of the lens unit 91 under control by the camera head controller 95.

The communication module 94 outputs signals transmitted from the control device 5 to the respective units in the camera head 9, such as the camera head controller 95. The communication module 94 converts information related to the current state of the camera head 9, and the like, into a signal format in accordance with a predetermined transmission method and outputs the converted signal to the control device 5 through the transmission cable 8. That is to say, the communication module 94 is a relay device that distributes the signals input from the control device 5 and the transmission cable 8 by, for example, serial-to-parallel conversion and outputs them to the respective units of the camera head 9, and collectively outputs the signals from the respective units of the camera head 9 to be output to the control device 5 and the transmission cable 8 by, for example, parallel-to-serial conversion.

The camera head controller 95 controls operations of the entire camera head 9 in accordance with a driving signal input through the transmission cable 8, an instruction signal output from an operation unit such as a switch provided on the outer surface of the camera head 9 in an exposed manner by a user operation onto the operation unit, and the like. The camera head controller 95 outputs the information related to the current state of the camera head 9 to the control device 5 through the transmission cable 8.

Each of the above-mentioned driving unit 93, communication module 94, and camera head controller 95 is implemented using a general processor such as a central processing unit (CPU) with an internal memory (not illustrated) recording therein programs or a dedicated processor like various types of operation circuits executing specific functions, such as an application specific integrated circuit (ASIC). Alternatively, each of them may be configured using an FPGA as one type of programmable integrated circuits. When each of them is configured by the FPGA, the FPGA as the programmable integrated circuit may be configured by configuration data read from a memory while the memory storing therein the configuration data is provided.

A signal processor that performs signal processing on the imaging signals generated by the communication module 94 and the imaging unit 92 may be configured in the camera head 9 and/or the transmission cable 8. Furthermore, an imaging clock for driving the imaging unit 92 and a driving clock for driving the driving unit 93 may be generated based on a reference clock generated by an oscillator (not illustrated) provided in the camera head 9 to be output to the imaging unit 92 and the driving unit 93, respectively. Alternatively, timing signals of various pieces of processing in the imaging unit 92, the driving unit 93, and the camera head controller 95 may be generated based on the synchronization signal input from the control device 5 through the transmission cable 8 and be output to the imaging unit 92, the driving unit 93, and the camera head controller 95, respectively. The camera head controller 95 may be provided not on the camera head 9 but on the transmission cable 8 or the control device 5.

Subsequently, the pieces of signal processing that the signal processor 51 and the image generator 52 of the control device 5 perform will be described. The signal processor 51 performs the signal processing such as the noise removal and, if necessary, the A/D conversion on the imaging signals generated in accordance with light corresponding to each observation method and outputs the digitized imaging signals (pulse signals) to the image generator 52.

Thereafter, the image generator 52 performs interpolation processing based on the imaging signals input from the signal processor 51 to generate color signals of respective color components of RGB and generate the image signal for display that the display device 4 displays. To be specific, in the normal observation, when the image generator 52 acquires electric signals of the green component that have been acquired by the G pixels and electric signals of the green component and the red component mixed therein that have been acquired by the W pixels from the second imaging element 922, it acquires signal values $S_R$ of the red component on the W pixels by interpolating signal values (signal values $S_G'$) of the green component on the W pixels from the signal values $S_G$ on the G pixels located around the W pixels and calculating the difference ($S_{GR}-S_G'$) between signal values $S_{GR}$ and the interpolated signal values $S_G'$ on the W pixels. Thereafter, the image generator 52 acquires signal values $S_R'$ of the red component at the G pixel positions from the acquired signal values $S_R$ of the red component at the W pixel positions. The image generator 52 acquires the signal values $S_R'$ of the red component at the G pixel positions from the signal values $S_R$ on the W pixels around the G pixels as described above. Furthermore, the image generator 52 generates color signals of the blue component based on electric signals generated by the respective pixels on the first imaging element 921 because the pixel arrangement of the first imaging element 921 and the pixel arrangement of the second imaging element 922 are identical to each other. In this manner, in the normal observation, the image generator 52 generates the color signals of the blue component based on the imaging signals acquired by the first imaging element 921, generates color signals of the green component having the signal values $S_G$ on the G pixels and the signal values $S_G'$ at the W pixel positions that are interpolated from the signal values $S_G$ among the imaging signals acquired by the second imaging element 922, and generates color signals of the red component having the signal values $S_R$ acquired from the signal values $S_{GR}$ and the signal values $S_G'$ on the W pixels and the signal values $S_R'$ at the G pixel positions that are interpolated from the signal values $S_R$. The image generator 52 generates the image signal (color image) for display based on the generated color signals (color images) of the respective color components. The image generator 52, for example, assigns the color signals of the red component to a red channel (hereinafter, R channel), assigns the color signals of the green component to a green channel (hereinafter, G channel), and assigns the color signals of the blue component to a blue channel (hereinafter, B channel).

In the NBI, the image generator 52 performs interpolation processing similar to that in the normal observation to generate color signals of the wavelength band Bn based on electric signals acquired by the first imaging element 921 and generate color signals of the wavelength band Gn based on electric signals acquired by the second imaging element 922. The image generator 52, for example, assigns the color signals of the wavelength band Bn to the G and B channels and assigns the color signals of the wavelength band Gn to the R channel.

Furthermore, in the IRI, the image generator 52 generates color signals of the wavelength band IR-1 based on electric signals of the wavelength band IR-1 that have been generated by the W pixels (and the G pixels) on the second imaging element 922, for example. The image generator 52 generates color signals of the wavelength band IR-2 based on electric signals of the wavelength band IR-2 that have been generated by the G pixels and the W pixels, for example. The image generator 52, for example, assigns the color signals of the wavelength band IR-1 to the R and G channels and assigns the color signals of the wavelength band IR-2 to the B channel.

Furthermore, in the AFI, the image generator 52 generates color signals of the wavelength band Ga-1 based on electric signals of the wavelength band Ca-1 that have been generated by the G pixels and the W pixels on the second imaging element 922. The image generator 52 generates color signals of the wavelength band Ga-2 based on electric signals of the wavelength band Ga-2 that have been generated by the W pixels (and the G pixels). The image generator 52, for example, assigns the color signals of the wavelength band Ga-1 to the R and B channels and assigns the color signals of the wavelength band Ga-2 to the G channel.

Furthermore, in the PDD, the image generator 52 generates color signals of the wavelength band Rp based on electric signals acquired by the first imaging element 921. The image generator 52 generates color signals of the wavelength band Bp by interpolating signal values on the G pixels based on electric signals acquired by the W pixels on the second imaging element 922. The image generator 52, for example, assigns the color signals of the wavelength band Rp to the R channel and assigns the color signals of the wavelength band Bp to the B channel.

As described above, the first imaging element 921 and the second imaging element 922 are provided with the first color filter 921a and the second color filter 922a, respectively, and the respective pixels $P_{xy}$ receive the light components of the wavelength bands corresponding to the filters. With this, even any observation method of the normal observation and the special light observations may acquire an image corresponding to each observation method without switching the imaging element and replacing the camera head.

With the above-mentioned first embodiment, the prism 923 separates the externally incident light selectively by the wavelength band of the blue component and the separated light components are made incident on the two imaging elements of the first imaging element 921 and the second imaging element 922. Furthermore, the first color filter 921a provided on the first imaging element 921 is formed by the B filters configured to transmit the light component of the wavelength band of blue and the second color filter 922a provided on the second imaging element 922 is formed by the G filters configured to transmit the light component of the wavelength band of green and the W filters configured to transmit the light component of the wavelength band of white. The B filters, the G filters, and the W filters are made to transmit the light component of the wavelength band of the infrared rays. With this configuration, a high-quality observation image may be acquired in each of the normal observation and the special light observations.

Moreover, with the above-mentioned first embodiment, the two imaging elements (the first imaging element 921 and the second imaging element 922) generate an image in each of the normal observation and the special light observations, thereby acquiring an image with higher image quality than an image that is acquired using a single-pate imaging element and reducing the size and weight in comparison with the case using the three-plate imaging elements.

In addition, with the above-mentioned first embodiment, the prism 923 separates light by reflection and transmission once for each. This light separation may simplify the configuration of the prism 923 and reduce it in size in comparison with a prism that outputs, to the outside, light components separated by being returned back a plurality of times, thereby reducing the entire apparatus in size and weight. Furthermore, reflection and transmission of the observation light to the output of the observation light from the incidence on the prism are made once for each as the minimum necessary time, thereby reducing attenuation of the observation light on the light paths to the first imaging element 921 and the second imaging element 922 and improving imaging sensitivity.

In the above-mentioned first embodiment, the color filter of the first imaging element 921 is formed by the B filters and the color filter of the second imaging element 922 is formed by the G filters and the W filters. Alternatively, the color filter of the first imaging element 921 may be formed by the G filters and the W filters and the color filter of the second imaging element 922 may be formed by the B filters by, for example, inversing the light wavelength bands that the prism 923 reflects and transmits from the above-mentioned wavelength bands.

In the above-mentioned first embodiment, the first imaging element 921 receives the light component through the first color filter 921a formed by the B filters. Alternatively, when the first imaging element 921 receives the light component of the wavelength band of a single color as in the first embodiment, the first imaging element 921 may directly receive the light component from the prism 923 without providing the first color filter 921a.

In the above-mentioned first embodiment, the prism 923 forms the cubic shape by bonding the two prisms having the triangular columnar shapes and the thin dichroic film 923a is provided between the bonded surfaces of the two prisms. Alternatively, a plate-like thin film mirror provided with a dichroic film may be used instead of the prism 923.

Subsequently, a modification of the first embodiment of the present disclosure will be described. Although the first color filter 921a provided on the first imaging element 921 is formed by the B filters configured to transmit the light component of the wavelength band of blue and the second color filter 922a provided on the second imaging element 922 is formed by the G filters configured to transmit the light component of the wavelength band of green and the W filters configured to transmit the light component of the wavelength band of white in the above-mentioned first embodiment, the combination of the filters is not limited thereto. Any combination of the filters that are arranged on the two imaging elements may be set as long as an image may be acquired in the normal observation and the special light observations.

First Modification of First Embodiment

FIG. 8 is a view for explaining a pixel array of an imaging element according to a first modification of the first embodiment of the present disclosure and is a view illustrating a filter array of a second color filter. An endoscope apparatus in the first modification includes a second color filter 922b instead of the second color filter 922a in the configuration of the above-mentioned endoscope apparatus 1. To be specific, the second color filter 922b has R filters instead of the G filters of the second color filter 922a.

Table 3 indicates light wavelength bands that the first imaging element 921 and the second imaging element 922 in the first modification acquire by the respective observation methods. To be specific, as indicated in Table 3, in the normal observation, the first imaging element 921 receives the light component of the wavelength band Bb of blue on the B pixels. The second imaging element 922 receives the light component of the wavelength band Rb of red on the R pixels and receives the light components of the wavelength band Gb of green and the wavelength band Rb of red on the W pixels.

TABLE 3

| OBSERVATION METHOD | PIXEL | BAND FIRST IMAGING ELEMENT | PIXEL | SECOND IMAGING ELEMENT | |
|---|---|---|---|---|---|
| NORMAL | B | Bb | R | | Rb |
| | | | W | Gb | Rb |
| NBI | B | Bn | R | — | |
| | | | W | Gn | |
| IRI | B | — | R | (IR-1) | IR-2 |
| | | | W | IR-1 | IR-2 |
| AFI | B | — | R | — | |
| | | | W | Ga-1 | Ga-2 |
| PDD | B | Bp | R | Rp | |
| | | | W | Rp | |

In the NBI, the first imaging element 921 receives the light component of the wavelength band Bn on the B pixels. The second imaging element 922 receives the light component of the wavelength band Gn on the W pixels.

In the IRI, the first imaging element 921 does not receive light. The second imaging element 922 receives the light component of the wavelength band IR-2 on the R pixels and receives the light components of the wavelength band IR-1 and the wavelength band IR-2 on the W pixels. The R pixels also receive the light component of the wavelength band IR-1 although sensitivity thereto is low.

In the AFI, the first imaging element 921 receives the light component of the wavelength band Ba on the B pixels but does not acquire signals thereof because it is not used for image generation. The second imaging element 922 separately receives the light component of the wavelength band Ga-1 and the light component of the wavelength band Ga-2 on the W pixels with illumination by the face sequential method.

In the PDD, the first imaging element 921 receives the light component of the wavelength band Bp on the B pixels.

The second imaging element 922 receives the light component of the wavelength band Rp on the R pixels and the W pixels.

In the first modification, the image generator 52 performs interpolation processing to generate color signals of respective color components of RGB and generate an image signal for display that the display device 4 displays in the same manner as the above-mentioned first embodiment. To be specific, in, for example, the normal observation, when the image generator 52 acquires electric signals of the red component that have been acquired by the R pixels and electric signals of the green component and the red component mixed therein that have been acquired by the W pixels from the second imaging element 922, it acquires signal values $S_G$ of the green component on the W pixels by interpolating signal values (signal values $S_R'$) of the red component on the W pixels from the signal values $S_R$ on the R pixels located around the W pixels and calculating the difference ($S_{GR}-S_R'$) between signal values $S_{GR}$ and the interpolated signal values $S_R'$ on the W pixels. Thereafter, the image generator 52 acquires signal values $S_G'$ of the green component at the R pixel positions from the acquired signal values $S_G$ of the green component at the W pixel positions. The image generator 52 acquires the signal values $S_G'$ of the green component at the R pixel positions from the signal values $S_G$ on the W pixels around the R pixels as described above.

In the IRI, the image generator 52 performs signal processing in the same manner as the first embodiment to generate color signals of the wavelength band IR-1 and color signals of the wavelength band IR-2. In the AFI, the image generator 52 generates color signals of the wavelength bands Ga-1 and Ga-2 by interpolating signal values of the respective wavelength bands on the R pixels based on electric signals of the wavelength bands Ga-1 and Ga-2 that have been generated by the W pixels.

In the NBI, the image generator 52 generates color signals of the wavelength band Bn based on acquired electric signals because the first imaging element 921 receives only the light component of the wavelength band Bn, and generates color signals of the wavelength band Gn by interpolating signal values of the wavelength band Gn on the R pixels because the W pixels on the second imaging element 922 receive only the light component of the wavelength band Gn. Furthermore, in the PDD, the image generator 52 generates color signals of the wavelength band Rp based on electric signals acquired by the second imaging element 922 because the R pixels and the W pixels receive the light component of the wavelength band Rp.

With the first modification, the red component may be largely acquired, thereby, in the PDD, providing an image with higher image quality than that in the above-mentioned first embodiment.

Second Modification of First Embodiment

FIG. 9 is a view for explaining a pixel array of an imaging element according to a second modification of the first embodiment of the present disclosure and is a view illustrating a filter array of a second color filter. An endoscope apparatus in the second modification includes a second color filter 922c instead of the second color filter 922a in the configuration of the above-mentioned endoscope apparatus 1. To be specific, the second color filter 922c has Cy filters configured to transmit light components of the wavelength bands of green and blue (light component of cyan) instead of the G filters of the second color filter 922a.

Figure 10:
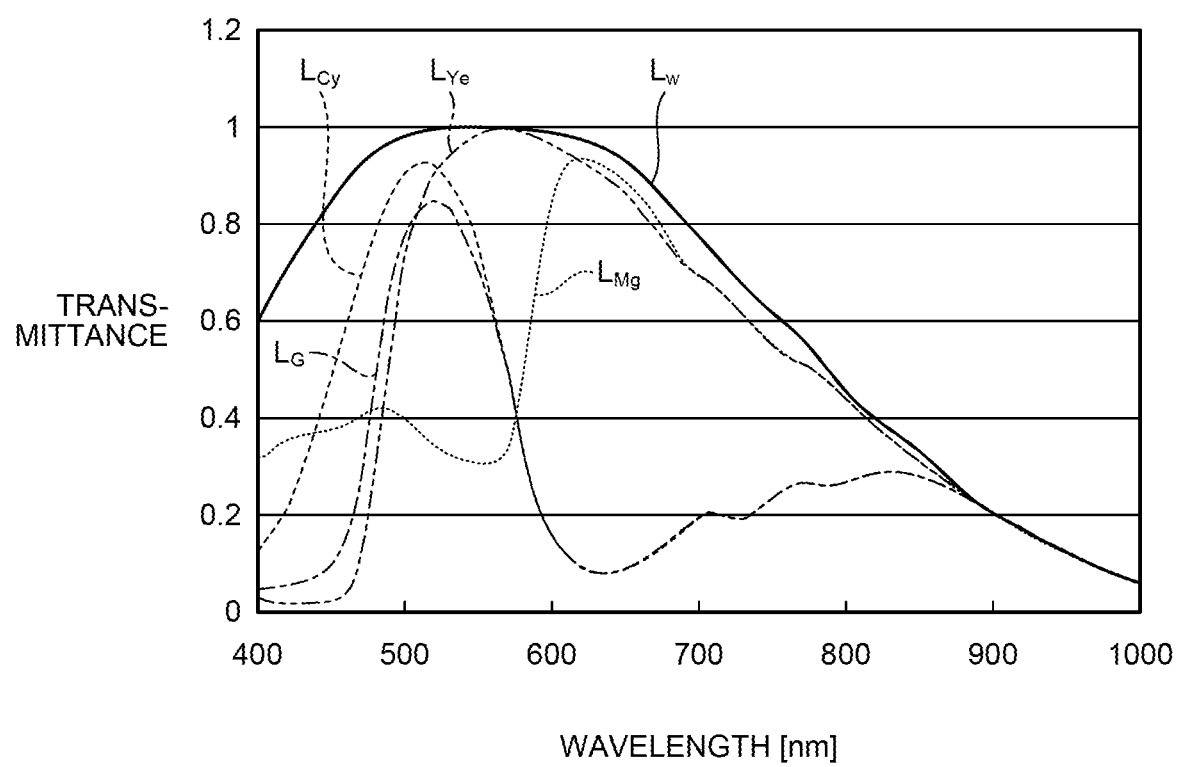
FIG. 10 is a view for explaining a wavelength band of a light component that a Cy filter of a color filter transmits in the second modification of the first embodiment of the present disclosure.

FIG. 10 is a view for explaining a wavelength band of the light component that the Cy filter of the color filter transmits in the second modification of the first embodiment of the present disclosure. FIG. 10 also illustrates, for explanation, transmission curves of the Cy filter, the G filter, the W filter, a Ye filter configured to transmit light components of the wavelength bands of red and green (light component of yellow), and an Mg filter configured to transmit light components of the wavelength bands of red and blue (light component of magenta). In FIG. 10, a curve $L_{Cy}$ indicates the transmission curve of the light component passing through the Cy filter, a curve $L_{Ye}$ indicates the transmission curve of the light component passing through the Ye filter, and a curve $L_{Mg}$ indicates the transmission curve of the light component passing through the Mg filter. As illustrated in FIG. 10, the respective filters in the second modification also have sensitivity to the wavelength band of the near infrared rays.

Table 4 indicates the light wavelength bands that the first imaging element 921 and the second imaging element 922 in the second modification acquire by the respective observation methods. To be specific, as indicated in Table 4, in the normal observation, the first imaging element 921 receives the light component of the wavelength band Bb of blue on the B pixels. The second imaging element 922 receives the light component of the wavelength band Gb of green on the Cy pixels and receives the light components of the wavelength band Gb of green and the wavelength band Rb of red on the W pixels.

TABLE 4

| OBSERVATION METHOD | PIXEL | BAND FIRST IMAGING ELEMENT | PIXEL | SECOND IMAGING ELEMENT | |
|---|---|---|---|---|---|
| NORMAL | B | Bb | Cy | | Gb |
| | | | W | Gb | Rb |
| NBI | B | Bn | Cy | | Gn |
| | | | W | | Gn |
| IRI | B | — | Cy | (IR-1) | IR-2 |
| | | | W | IR-1 | IR-2 |
| AFI | B | — | Cy | Ga-1 | (Ga-2) |
| | | | W | Ga-1 | Ga-2 |
| PDD | B | Bp | Cy | | — |
| | | | W | | Rp |

In the NBI, the first imaging element 921 receives the light component of the wavelength band Bn on the B pixels. The second imaging element 922 receives the light component of the wavelength band Gn on the Cy pixels and the W pixels.

In the IRI, the first imaging element 921 does not receive light. The second imaging element 922 receives the light component of the wavelength band IR-2 on the Cy pixels and receives the light components of the wavelength band IR-1 and the wavelength band IR-2 on the W pixels. The Cy pixels also receive the light component of the wavelength band IR-1 although sensitivity thereto is low.

In the AFI, the first imaging element 921 receives the light component of the wavelength band Ba on the B pixels but does not acquire signals thereof because it is not used for image generation. The second imaging element 922 receives the light component of the wavelength band Ga-1 on the Cy pixels and receives the light components of the wavelength band Ga-1 and the wavelength band Ga-2 on the W pixels. The Cy pixels also receive the light component of the wavelength band Ga-2 although sensitivity thereto is low.

In the PDD, the first imaging element 921 receives the light component of the wavelength band Bp on the B pixels. The second imaging element 922 receives the light component of the wavelength band Rp on the W pixels.

In the second modification, the image generator 52 performs interpolation processing to generate color signals of respective color components of RGB and generate an image signal for display that the display device 4 displays in the same manner as the above-mentioned first embodiment. To be specific, in, for example, the normal observation, when the image generator 52 acquires electric signals of the green component that have been acquired by the Cy pixels and electric signals of the green component and the red component mixed therein that have been acquired by the W pixels from the second imaging element 922, it acquires signal values $S_R$ of the red component on the W pixels by interpolating signal values (signal values $S_G'$) of the green component on the W pixels from the signal values $S_G$ on the Cy pixels located around the W pixels and calculating the difference ($S_{GR}-S_G'$) between signal values $S_{GR}$ and the interpolated signal values $S_G'$ on the W pixels. Thereafter, the image generator 52 acquires signal values $S_R'$ of the red component at the Cy pixel positions from the acquired signal values $S_R$ of the red component at the W pixel positions.

In the IRI, the image generator 52 performs signal processing similar to that in the above-mentioned first embodiment to generate color signals of the wavelength band IR-1 and color signals of the wavelength band IR-2. In the AFI, the image generator 52 generates color signals of the wavelength band Ga-1 and color signals of the wavelength band Ga-2.

In the NBI, the image generator 52 generates color signals of the wavelength band Bn based on acquired electric signals because the first imaging element 921 receives only the light component of the wavelength band Bn and generates color signals of the wavelength band Gn based on electric signals acquired by the second imaging element 922 because the Cy pixels and the W pixels on the second imaging element 922 receive only the light component of the wavelength band Gn. Furthermore, in the PDD, the image generator 52 generates color signals of the wavelength band Rp by interpolating signal values on the Cy pixels because the W pixels receive the light component of the wavelength band Rp.

Third Modification of First Embodiment

FIG. 11 is a view for explaining a pixel array of an imaging element according to a third modification of the first embodiment of the present disclosure and is a view illustrating a filter array of a first color filter. FIG. 12 is a view for explaining the pixel array of the imaging element in the third modification of the first embodiment of the present disclosure and is a view illustrating a filter array of a second color filter. An endoscope apparatus in the third modification includes a first color filter 921b and a second color filter 922d instead of the first color filter 921a and the second color filter 922a in the configuration of the above-mentioned endoscope apparatus 1. To be specific, the first color filter 921b has G filters configured to transmit the light component of the wavelength band of green instead of the B filters of the first color filter 921a. The second color filter 922d has B filters configured to transmit the light component of the wavelength band of blue instead of the G filters of the second color filter 922a. In the third modification, the dichroic film of the prism 923 reflects the light component of the wavelength band of green.

Table 5 indicates the light wavelength bands that the first imaging element 921 and the second imaging element 922 in the third modification acquire by the respective observation methods. To be specific, as indicated in Table 5, in the normal observation, the first imaging element 921 receives the light component of the wavelength band Gb of green on the G pixels. The second imaging element 922 receives the light component of the wavelength band Bb of blue on the B pixels and receives the light components of the wavelength band Bb of blue and the wavelength band Rb of red on the W pixels.

TABLE 5

| OBSERVATION METHOD | PIXEL | FIRST IMAGING ELEMENT | PIXEL | SECOND IMAGING ELEMENT | |
|---|---|---|---|---|---|
| NORMAL | G | Gb | B | Bb | |
|  |  |  | W | Rb | Bb |
| NBI | G | Gn | B | Bn | |
|  |  |  | W | Bn | |
| IRI | G | — | B | (IR-1) | IR-2 |
|  |  |  | W | IR-1 | IR-2 |
| AFI | G | Ga-1  Ga-2 | B | — | |
|  |  |  | W | — | |
| PDD | G | — | B | Bp | |
|  |  |  | W | Rp | Bp |

In the NBI, the first imaging element 921 receives the light component of the wavelength band Gn on the G pixels. The second imaging element 922 receives the light component of the wavelength band Bn on the B pixels and the W pixels.

In the IRI, the first imaging element 921 does not receive light. The second imaging element 922 receives the light component of the wavelength band IR-2 on the B pixels and receives the light components of the wavelength band IR-1 and the wavelength band IR-2 on the W pixels. The B pixels also receive the light component of the wavelength band IR-1 although sensitivity thereto is low.

In the AFI, the first imaging element 921 receives the light components of the wavelength band Ga-1 and the wavelength band Ga-2 on the G pixels. On the other hand, the second imaging element 922 receives the light component of the wavelength band Ba on the B pixels and the W pixels but does not acquire signals thereof because it is not used for image generation.

In the PDD, the first imaging element 921 does not receive light. On the other hand, the second imaging element 922 receives the light component of the wavelength band Bp on the B pixels and receives the light components of the wavelength bands Bp and Rp on the W pixels.

In the third modification, the image generator 52 performs interpolation processing to generate color signals of respective color components of RGB and generate an image signal for display that the display device 4 displays in the same manner as the above-mentioned first embodiment. To be specific, in, for example, the normal observation, when the image generator 52 acquires electric signals of the blue component that have been acquired by the B pixels and electric signals of the blue component and the red component mixed therein that have been acquired by the W pixels from the second imaging element 922, it acquires signal values $S_R$ of the red component on the W pixels by interpolating signal values (signal values $S_R'$) of the blue component on the W pixels from the signal values $S_B$ on the B pixels located around the W pixels and calculating the difference ($S_{BR}-S_B'$) between signal values $S_{BR}$ and the interpolated signal values $S_R'$ on the W pixels. Thereafter, the image generator 52 acquires signal values $S_R'$ of the red component at the B pixel positions from the acquired signal values $S_R$ of the red component at the W pixel positions. The image generator 52 acquires the signal values $S_R'$ of the red component at the B pixel positions from the signal values $S_R$ on the W pixels located around the B pixels as described above.

In the IRI, the image generator 52 performs signal processing similar to that in the above-mentioned first embodiment to generate color signals of the wavelength band IR-1 and color signals of the wavelength band IR-2 based on electric signals generated by the B pixels and the W pixels, for example. In the AFI, the image generator 52 generates color signals of the wavelength bands Ga-1 and Ga-2 based on electric signals of the wavelength bands Ga-1 and Ga-2 that have been generated by the G pixels, respectively.

In the NBI, the image generator 52 generates color signals of the wavelength band Gn based on acquired electric signals because the first imaging element 921 receives only the light component of the wavelength band Gn, and generates color signals of the wavelength band Bn based on electric signals acquired by the second imaging element 922 because the B pixels and the W pixels on the second imaging element 922 receive only the light component of the wavelength band Bn. Furthermore, in the PDD, the image generator 52 generates color signals of the wavelength band Bp by interpolating signal values of the wavelength band Bp on the W pixels and generates color signals of the wavelength band Rp by acquiring signal values of the wavelength band Rp by calculation of the difference and interpolation because the B pixels on the second imaging element 922 receive the light component of the wavelength band Bp and the W pixels thereon receive the light components of the wavelength bands Bp and Rp.

In the third modification, the entire single plate acquires the green component because human feels green light brightly with visibility characteristics of human eyes, thereby providing an image with higher quality than that in the above-mentioned first embodiment in the normal observation and the like.

Fourth Modification of First Embodiment

In the above-mentioned third modification, the second color filter 922d may be the second color filter 922c illustrated in FIG. 9. An endoscope apparatus in the fourth modification includes the second color filter 922c instead of the second color filter 922d in the configuration in the above-mentioned third modification. In the fourth modification, the dichroic film of the prism 923 reflects the light component of the wavelength band of green.

Table 6 indicates the light wavelength bands that the first imaging element 921 and the second imaging element 922 in the fourth modification acquire by the respective observation methods. To be specific, as indicated in Table 6, in the normal observation, the first imaging element 921 receives the light component of the wavelength band Gb of green on the G pixels. The second imaging element 922 receives the light component of the wavelength band Bb of blue on the Cy pixels and receives the light components of the wavelength band Bb of blue and the wavelength band Rb of red on the W pixels.

TABLE 6

| OBSERVATION METHOD | PIXEL | FIRST IMAGING ELEMENT | | PIXEL | SECOND IMAGING ELEMENT | |
|---|---|---|---|---|---|---|
| NORMAL | G | Gb | | Cy | Bb | |
|  |  |  |  | W | Rb | Bb |
| NBI | G | Gn | | Cy | Bn | |
|  |  |  |  | W | Bn | |
| IRI | G | — | | Cy | (IR-1) | IR-2 |
|  |  |  |  | W | IR-1 | IR-2 |
| AFI | G | Ga-1 | Ga-2 | Cy | — | |
|  |  |  |  | W | — | |
| PDD | G | — | | Cy | Bp | |
|  |  |  |  | W | Rp | Bp |

In the NBI, the first imaging element 921 receives the light component of the wavelength band Gn on the G pixels. The second imaging element 922 receives the light component of the wavelength band Bn on the Cy pixels and the W pixels.

In the IRI, the first imaging element 921 does not receive light. The second imaging element 922 receives the light component of the wavelength band IR-2 on the Cy pixels and receives the light components of the wavelength band IR-1 and the wavelength band IR-2 on the W pixels. The Cy pixels also receive the light component of the wavelength band IR-1 although sensitivity thereto is low.

In the AFI, the first imaging element 921 receives the light components of the wavelength band Ga-1 and the wavelength band Ga-2 on the G pixels. On the other hand, the second imaging element 922 receives the light component of the wavelength band Ba on the Cy pixels and the W pixels but does not acquire signals thereof because it is not used for image generation.

In the PDD, the first imaging element 921 does not receive light. On the other hand, the second imaging element 922 receives the light component of the wavelength band Bp on the Cy pixels and receives the light components of the wavelength bands Bp and Rp on the W pixels.

In the fourth modification, the image generator 52 performs interpolation processing to generate color signals of respective color components of RGB and generate an image signal for display that the display device 4 displays in the same manner as the above-mentioned first embodiment. To be specific, in, for example, the normal observation, when the image generator 52 acquires electric signals of the blue component that have been acquired by the Cy pixels and electric signals of the blue component and the red component mixed therein that have been acquired by the W pixels from the second imaging element 922, it acquires signal values $S_R$ of the red component on the W pixels by interpolating signal values (signal values $S_{Cy}'$) of the blue component on the W pixels from the signal values $S_{Cy}$ on the Cy pixels located around the W pixels and calculating the difference ($S_{CyR}-S_{Cy}'$) between signal values $S_{CyR}$ and the interpolated signal values $S_{Cy}'$ on the W pixels. Thereafter, the image generator 52 acquires signal values $S_R'$ of the red component at the B pixel positions from the acquired signal values $S_R$ of the red component at the W pixel positions. The image generator 52 acquires the signal values $S_R'$ of the red component at the Cy pixel positions from the signal values $S_R$ on the W pixels located around the Cy pixels as described above.

In the IRI, the image generator 52 performs signal processing similar to that in the above-mentioned first embodiment to generate color signals of the wavelength band IR-1 and color signals of the wavelength band IR-2 based on electric signals generated by the Cy pixels and the W pixels, for example. In the AFI, the image generator 52 generates color signals of the wavelength bands Ga-1 and Ga-2 based on electric signals of the wavelength bands Ga-1 and Ga-2 that have been generated by the G pixels.

In the NBI, the image generator 52 generates color signals of the wavelength band Gn based on acquired electric signals because the first imaging element 921 receives only the light component of the wavelength band Gn and generates color signals of the wavelength band Bn based on electric signals acquired by the second imaging element 922 because the Cy pixels and the W pixels on the second imaging element 922 receive only the light component of the wavelength band Bn. Furthermore, in the PDD, the image generator 52 generates color signals of the blue component by interpolating signal values of the wavelength band Bp on the W pixels and generates color signals of the wavelength band Rp by acquiring signal values of the wavelength band Rp by calculation of the difference and interpolation because the Cy pixels receive the light component of the wavelength band Bp and the W pixels receive the light components of the wavelength bands Bp and Rp.

Fifth Modification of First Embodiment

Figure 13:
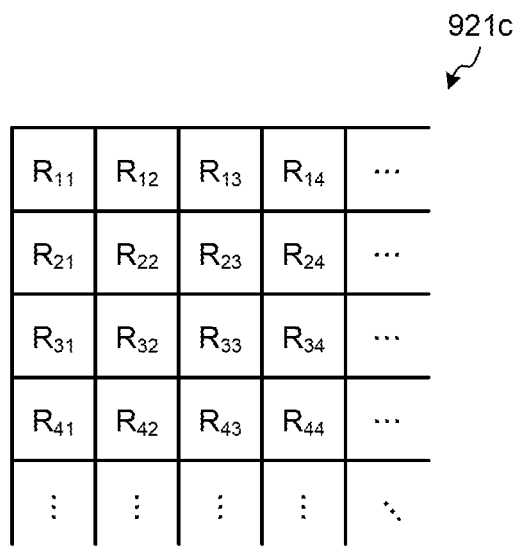
FIG. 13 is a view for explaining a pixel array of an imaging element according to a fifth modification of the first embodiment of the present disclosure.

FIG. 13 is a view for explaining a pixel array of an imaging element according to a fifth modification of the first embodiment of the present disclosure, and is a view illustrating a filter array of a first color filter. An endoscope apparatus in the fifth modification includes a first color filter 921c instead of the first color filter 921a in the configuration of the above-mentioned endoscope apparatus 1. To be specific, the first color filter 921c has R filters instead of the G filters of the first color filter 921a. In the fifth modification, the dichroic film of the prism 923 reflects the light component of the wavelength band of red.

Table 7 indicates the light wavelength bands that the first imaging element 921 and the second imaging element 922 in the fifth modification acquire by the respective observation methods. To be specific, as indicated in Table 7, in the normal observation, the first imaging element 921 receives the light component of the wavelength band Rb of red on R pixels. The second imaging element 922 receives the light component of the wavelength band Gb of green on the G pixels and receives the light components of the wavelength band Gb of green and the wavelength band Bb of blue on the W pixels.

TABLE 7

| OBSERVATION METHOD | PIXEL | FIRST IMAGING ELEMENT | PIXEL | SECOND IMAGING ELEMENT | | NOTE |
|---|---|---|---|---|---|---|
| NORMAL | R | Rb | G | Gb | | |
| | | | W | Gb | Bb | |
| NBI | R | — | G | Gn | | |
| | | | W | Gn | Bn | |
| IRI | R | — | G | (IR-1) | IR-2 | |
| | | | W | IR-1 | IR-2 | |

TABLE 7-continued

| OBSERVATION METHOD | PIXEL | FIRST IMAGING ELEMENT | PIXEL | SECOND IMAGING ELEMENT | | NOTE |
|---|---|---|---|---|---|---|
| AFI | R | — | G | Ga-1 | (Ga-2) | FILTER FOR CUTTING WAVELENGTH BAND Ba IS PROVIDED AT LIGHT RECEIVING SIDE |
| | | | W | Ga-1 | Ga-2 | |
| PDD | R | Rp | G | — | | |
| | | | W | Bp | | |

In the NBI, the first imaging element 921 does not receive light. The second imaging element 922 receives the light component of the wavelength band Gn on the G pixels and receives the light components of the wavelength bands Gn and Bn on the W pixels.

In the IRI, the first imaging element 921 does not receive light. The second imaging element 922 receives the light component of the wavelength band IR-2 on the G pixels and receives the light components of the wavelength band IR-1 and the wavelength band IR-2 on the W pixels. The G pixels also receive the light component of the wavelength band IR-1 although sensitivity thereto is low.

In the AFI, the first imaging element 921 does not receive light. The second imaging element 922 receives the light component of the wavelength band Ga-1 on the G pixels and receives the light components of the wavelength band Ga-1 and the wavelength band Ga-2 on the W pixels. The G pixels also receive the light component of the wavelength band Ga-2 although sensitivity thereto is low. In the fifth modification, the second color filter 922a is provided with a barrier filter so as to prevent the light component of the wavelength band Ba from being incident thereon.

In the PDD, the first imaging element 921 receives the light component of the wavelength band Rp on the R pixels. The second imaging element 922 receives the light component of the wavelength band Bp on the W pixels.

In the fifth modification, the image generator 52 performs interpolation processing to generate color signals of respective color components of RGB and generate an image signal for display that the display device 4 displays in the same manner as the above-mentioned first embodiment. To be specific, in, for example, the normal observation, when the image generator 52 acquires electric signals of the green component that have been acquired by the G pixels and electric signals of the green component and the blue component mixed therein that have been acquired by the W pixels from the second imaging element 922, it acquires signal values $S_B$ of the blue component on the W pixels by interpolating signal values (signal values $S_G'$) of the green component on the W pixels from the signal values $S_G$ on the G pixels located around the W pixels and calculating the difference ($S_{GB}-S_G'$) between signal values $S_{GB}$ and the interpolated signal values $S_G'$ on the W pixels. Thereafter, the image generator 52 acquires signal values $S_B'$ of the blue component at the G pixel positions from the acquired signal values $S_B$ of the blue component at the W pixel positions. The image generator 52 acquires the signal values $S_B'$ of the blue component at the G pixel positions from the signal values $S_B$ on the W pixels around the G pixels as described above.

In the IRI, the image generator 52 performs signal processing in the same manner as the above-mentioned first embodiment to generate color signals of the wavelength band IR-1 and color signals of the wavelength band IR-2 based on electric signals generated by the G pixels and the W pixels, for example. In the AFI, the image generator 52 generates color signals of the wavelength band Ga-1 and color signals of the wavelength band Ga-2 based on electric signals generated by the G pixels and the W pixels.

In the NBI, the image generator 52 generates color signals of the wavelength band Gn by interpolating signal values of the wavelength band Gn on the W pixels and generates color signals of the wavelength band Bn by acquiring signal values of the wavelength band Bn by calculation of the difference and interpolation because the G pixels on the second imaging element 922 receive the light component of the wavelength band Gn and the W pixels thereon receive the light components of the wavelength bands Gn and Bn. Furthermore, in the PDD, the image generator 52 generates color signals of the wavelength band Rp based on acquired electric signals because the first imaging element 921 receives only the light component of the wavelength band Rp, and generates color signals of the wavelength band Bp by performing the interpolation processing based on electric signals acquired by the W because the W pixels on the second imaging element 922 receive only the light component of the wavelength band Bp.

Sixth Modification of First Embodiment

Figure 14:
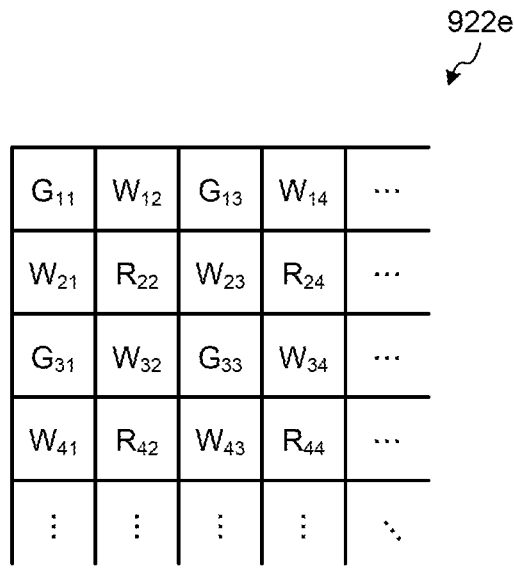
FIG. 14 is a view for explaining a pixel array of an imaging element according to a sixth modification of the first embodiment of the present disclosure.

FIG. 14 is a view for explaining a pixel array of an imaging element according to a sixth modification of the first embodiment of the present disclosure, and is a view illustrating a filter array of a second color filter. An endoscope apparatus in the sixth modification includes a second color filter 922e instead of the second color filter 922a in the configuration of the above-mentioned endoscope apparatus 1. To be specific, the W filters are arranged on the second color filter 922e in a grid form and the G filters and the R filters are alternately arranged row by row. On the second color filter 922e, the W filters and the G filters or the W filters and the R filters are alternately arranged in the row direction.

Table 8 indicates light wavelength bands that the first imaging element 921 and the second imaging element 922 in the sixth modification acquire by the respective observation methods. To be specific, as indicated in Table 8, in the normal observation, the first imaging element 921 receives the light component of the wavelength band Bb of blue on the B pixels. The second imaging element 922 receives the light component of the wavelength band Rb of red on the R pixels, receives the light component of the wavelength band Gb of green on the G pixels, and receives the light components of the wavelength band Gb of green and the wavelength band Rb of red on the W pixels.

TABLE 8

| OBSERVA-TION METHOD | PIXEL | FIRST IMAGING ELEMENT | PIXEL | SECOND IMAGING ELEMENT | |
|---|---|---|---|---|---|
| NORMAL | B | Bb | G | Gb | |
| | | | R | Rb | |
| | | | W | Gb | Rb |

TABLE 8-continued

| OBSERVA-TION METHOD | PIXEL | FIRST IMAGING ELEMENT | PIXEL | SECOND IMAGING ELEMENT | |
|---|---|---|---|---|---|
| NBI | B | Bn | G | Gn | |
| | | | R | — | |
| | | | W | Gn | |
| IRI | B | — | G | (IR-1) | IR-2 |
| | | | R | IR-1 | IR-2 |
| | | | W | IR-1 | IR-2 |
| AFI | B | — | G | Ga-1 | (Ga-2) |
| | | | R | — | |
| | | | W | Ga-1 | Ga-2 |
| PDD | B | Bp | G | — | |
| | | | R | Rp | |
| | | | W | Rp | |

In the NBI, the first imaging element 921 receives the light component of the wavelength band Bn on the B pixels. The second imaging element 922 receives the light component of the wavelength band Gn on the G pixels and the W pixels.

In the IRI, the first imaging element 921 does not receive light. The second imaging element 922 receives the light component of the wavelength band IR-2 on the G pixels and receives the light components of the wavelength band IR-1 and the wavelength band IR-2 on the W pixels. The G pixels also receive the light component of the wavelength band IR-1 although sensitivity thereto is low.

In the AFI, the first imaging element 921 receives the light component of the wavelength band Ba on the B pixels but does not acquire signals thereof because it is not used for image generation. The second imaging element 922 receives the light component of the wavelength band Ga-1 on the G pixels and receives the light components of the wavelength band Ga-1 and the wavelength band Ga-2 on the W pixels. The G pixels also receive the light component of the wavelength band Ga-2 although sensitivity thereto is low.

In the PDD, the first imaging element 921 receives the light component of the wavelength band Bp on the B pixels. The second imaging element 922 does not receive light on the G pixels and receives the light component of the wavelength band Rp on the R pixels and the W pixels.

In the sixth modification, the image generator 52 performs interpolation processing to generate color signals of respective color components of RGB and generate an image signal for display that the display device 4 displays in the same manner as the above-mentioned first embodiment. To be specific, in, for example, the normal observation, when the image generator 52 acquires electric signals of the green component that have been acquired by the G pixels, electric signals of the red component that have been acquired by the R pixels, and electric signals of the green component and the red component mixed therein that have been acquired by the W pixels from the second imaging element 922, it acquires signal values $S_R$ of the red component on the W pixels by interpolating signal values (signal values $S_G'$) of the green component on the W pixels from the signal values $S_G$ on the G pixels located around the W pixels and calculating the difference ($S_{CR}-S_C'$) between signal values $S_{GR}$ and the interpolated signal values $S_G'$ on the W pixels. Furthermore, the image generator 52 acquires signal values $S_G'$ of the green component at the R pixel positions from the signal values $S_G$ of the G pixels located around the R pixels.

In the IRI, the image generator 52 performs signal processing similar to that in the above-mentioned first embodiment to generate color signals of the wavelength band IR-1 and color signals of the wavelength band IR-2 based on electric signals generated by the G pixels, the R pixels, and the W pixels, for example. In the AFI, the image generator 52 generates color signals of the wavelength band Ga-1 and color signals of the wavelength band Ga-2 by interpolating signal values on the R pixels based on electric signals generated by the G pixels and the W pixels.

In the NBI, the image generator 52 generates color signals of the wavelength band Bn based on acquired electric signals because the first imaging element 921 receives only the light component of the wavelength band Bn, and generates color signals of the wavelength band Gn by interpolating signal values of the wavelength band Gn on the R pixels because the G pixels and the W pixels on the second imaging element 922 receive only the light component of the wavelength band Gn. Furthermore, in the PDD, the image generator 52 generates color signals of the wavelength band Bp based on electric signals acquired by the first imaging element 921, and generates color signals of the wavelength band Rp based on electric signals acquired by the respective pixels because the R pixels and the W pixels receive the light component of the wavelength band Rp.

In the sixth modification, the signal values of the red component are acquired alone by providing the R filters on the second color filter unlike the filters of the second color filter 922a in the above-mentioned first embodiment, thereby, in the normal observation and the like, providing an image with improved color reproducibility rather than that in the above-mentioned first embodiment.

As described above, also in the first to the sixth modifications, the first imaging element 921 and the second imaging element 922 are provided with the first color filter and the second color filter, respectively, and the respective pixels $P_{xy}$ receive the light components of the wavelength bands corresponding to the filters. With this, even any observation method of the normal observation and the special light observations may acquire an image corresponding to each observation method without switching the imaging element and replacing the camera head.

Second Embodiment

Figure 15:
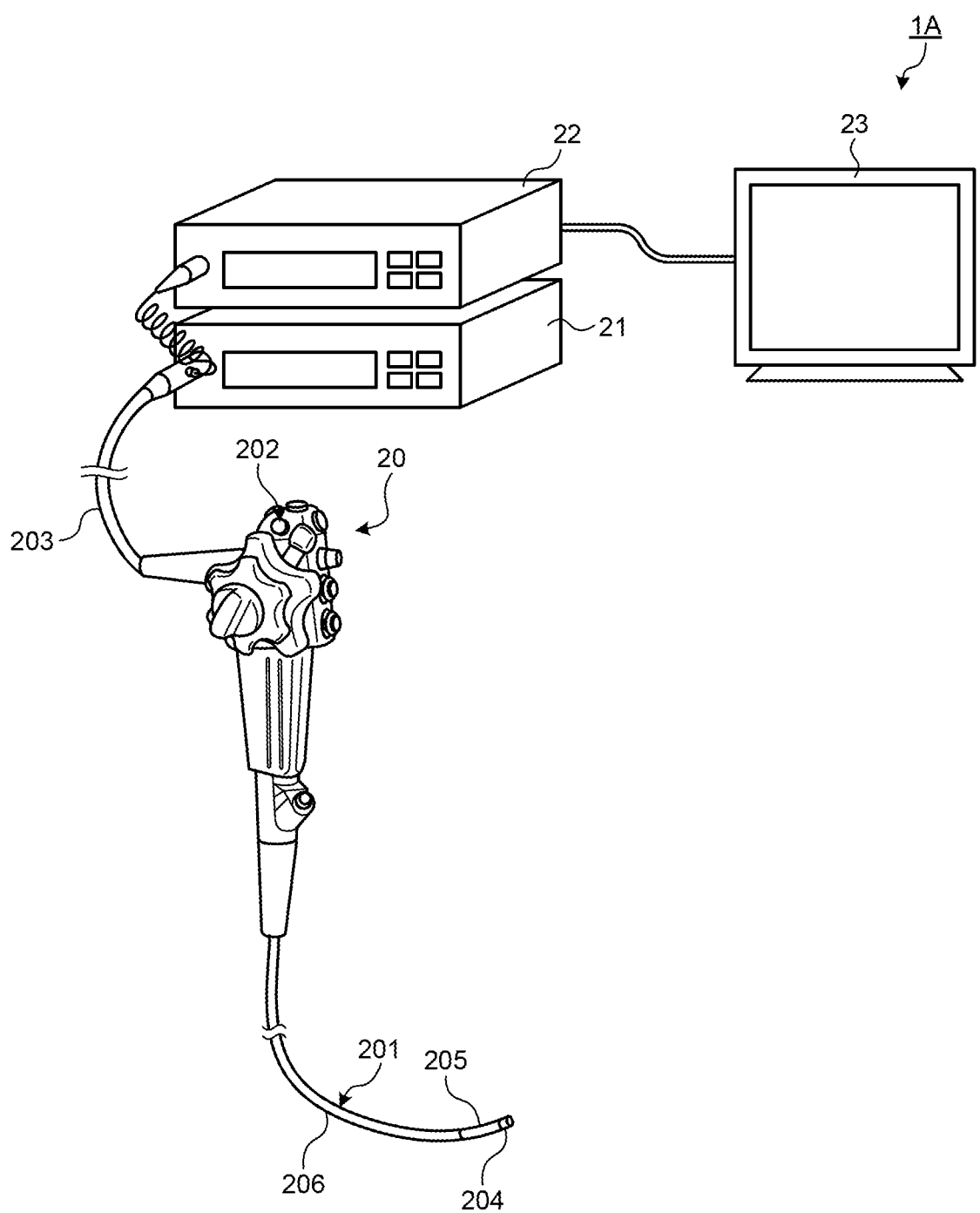
FIG. 15 is a view illustrating the schematic configuration of an endoscope apparatus according to a second embodiment of the present disclosure.

Subsequently, a second embodiment of the present disclosure will be described. FIG. 15 is a view illustrating the schematic configuration of an endoscope apparatus 1A in the second embodiment of the present disclosure. Although the endoscope apparatus 1 using the rigid scope as the endoscope 2 has been described in the above-mentioned first embodiment, the endoscope apparatus is not limited thereto and an endoscope apparatus using a flexible scope as the endoscope 2 may be configured. In the second embodiment, an imaging unit is provided on the leading end of an insertion portion of the flexible endoscope as an example.

The endoscope apparatus 1A includes an endoscope 20 that images in-vivo images at an observation site by inserting an insertion portion 201 into a subject to generate electric signals, a light source device 21 that generates illumination light to be output from the leading end of the endoscope 20, a control device 22 that performs predetermined image processing on the electric signals acquired by the endoscope 20 and collectively controls operations of the entire endoscope apparatus 1A, and a display device 23 that displays the in-vivo images on which the control device 22 has performed the image processing. The endoscope apparatus 1A acquires the in-vivo images in the subject by inserting the insertion portion 201 into the subject such as a patient. The light source device 21 includes the above-mentioned light source unit 61, wavelength selector 62, and driving unit 63. The control device 22 has the functions of the above-mentioned signal processor 51, image generator 52, mode setting unit 55, and the like.

The endoscope 20 includes the insertion portion 201 that has flexibility and forms an elongated shape, an operation unit 202 that is connected to the base end side of the insertion portion 201 and receives input of various operation signals, and a universal code 203 that extends from the operation unit 202 in the direction different from the extension direction of the insertion portion 201 and incorporates therein various cables connected to the light source device 21 and the control device 22.

The insertion portion 201 includes a leading end portion 204 that incorporates therein an imaging unit 92a in the second embodiment, a bent portion 205 that is configured by a plurality of bending pieces and may be freely bent, and a long flexible tube portion 206 that is connected to the base end side of the bent portion 205 and has flexibility.

Figure 16:
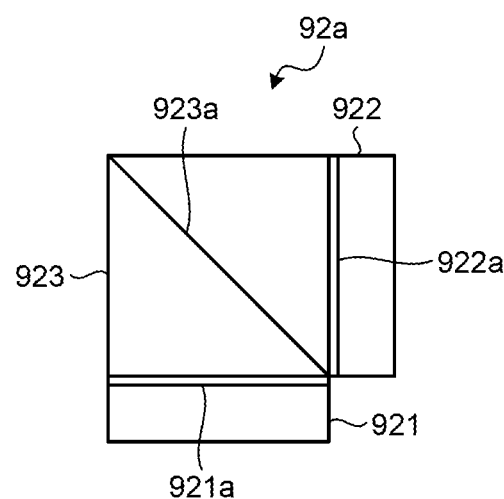
FIG. 16 is a schematic plan view for explaining the configuration of an imaging unit in the second embodiment of the present disclosure.

FIG. 16 is a schematic plan view for explaining the configuration of the imaging unit in the second embodiment of the present disclosure. The imaging unit 92a includes the first imaging element 921 provided with the above-mentioned first color filter 921a and the like, the second imaging element 922 provided with the above-mentioned second color filter 922a and the like, and the prism 923 as in the imaging unit 92. In the imaging unit 92a, the respective light receiving surfaces (the first color filter 921a and the second color filter 922a) of the first imaging element 921 and the second imaging element 922 are arranged on different surfaces of the prism 923. The surfaces of the prism 923 on which the first imaging element 921 and the second imaging element 922 are arranged are preferably orthogonal to each other.

Usage of a thin film substrate such as an FPC substrate for electrically connecting the first imaging element 921 and the second imaging element 922 to the communication module 94 and the like may further reduce the imaging unit 92a in thickness.

Usage of the imaging unit 92a in the second embodiment may prevent increase of the insertion portion 201 in diameter even when two-plate-type imaging elements are provided on the leading end portion 204 of the insertion portion 201 of the flexible endoscope.

Third Embodiment

Figure 17:
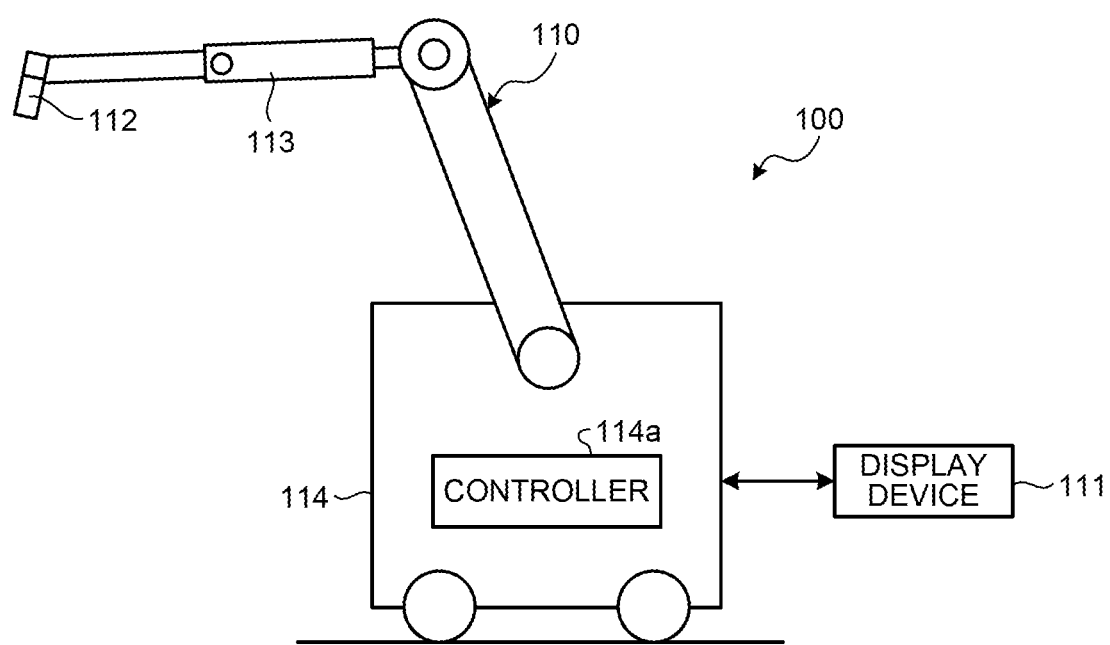
FIG. 17 is a view schematically illustrating the overall configuration of a microscope system for surgery as a medical observation system including a medical imaging device according to a third embodiment of the present disclosure.

Next, a third embodiment of the present disclosure will be described. FIG. 17 is a view schematically illustrating the overall configuration of a microscope system for surgery as a medical observation system including a medical imaging device in the third embodiment. Although the rigid endoscope has been described as an example in the above-mentioned first embodiment, the microscope system for surgery (medical image acquisition system) that has functions of imaging a predetermined visual field region in an enlarged manner and displaying the imaged image will be described as an example in the third embodiment.

A microscope system for surgery 100 includes a microscope device 110 as a medical imaging device that acquires an image for observing a subject by imaging and a display device 111 that displays the image imaged by the microscope device 110. The display device 111 may also be configured integrally with the microscope device 110.

The microscope device 110 includes a microscope unit 112 that images a microfine site of the subject in an enlarged manner, a support portion 113 that is connected to a base end portion of the microscope unit 112 and has an arm supporting the microscope unit 112 in a rotationally movable manner, and a base portion 114 that holds a base end portion of the support portion 113 in a rotationally movable manner and is movable on a floor surface. The base portion 114 includes a controller 114a that controls operations of the microscope system for surgery 100. The base portion 114 may not be provided on the floor surface in a movable manner but may be fixed to a ceiling, a wall surface, or the like to support the support portion 113. The base portion 114 may include a light source unit that generates illumination light to be emitted to the subject from the microscope device 110.

The microscope unit 112 forms, for example, a cylindrical shape, and includes the above-mentioned imaging unit 92 in the cylinder. A switch for receiving input of an operation instruction of the microscope device 110 is provided on the side surface of the microscope unit 112. A cover glass (not illustrated) for protecting the interior is provided on an opening surface on a lower end portion of the microscope unit 112.

A user such as a technician moves the microscope unit 112 and performs a zoom operation while operating various switches in a state of gripping the microscope unit 112. The microscope unit 112 preferably has an elongated shape extending in the observation direction such that the user may easily grip it and change the visual field direction. The microscope unit 112 may therefore have a shape other than the cylindrical shape and may be, for example, a polygonal shape.

The above-mentioned imaging unit 92 is provided on the microscope unit 112 of the microscope system for surgery 100 having the above-mentioned configuration, thereby preventing increase of the microscope unit 112 in diameter.

Although the modes for carrying out the present disclosure have been described hereinbefore, the present disclosure is not limited only by the above-mentioned embodiments. Although the control device 5 performs the signal processing and the like in the above-mentioned embodiments, the camera head 9 may perform the signal processing and the like.

As described above, the medical imaging device, the medical image acquisition system, and the endoscope apparatus according to the present disclosure are useful for acquiring an observation image with high quality while preventing increase of the apparatus in size and weight.

The present disclosure provides an effect of acquiring the observation image with high quality while preventing increase of the apparatus in size and weight.

It should be understood by those skilled in the art that various modifications, combinations, sub-combinations and alterations may occur depending on design requirements and other factors insofar as they are within the scope of the appended claims or the equivalents thereof.

What is claimed is:

1. A medical imaging device comprising:
  optics that separate light from an outside into a first light component of a wavelength band of any one color among wavelength bands of red, green, and blue and a second light component containing light components of wavelength bands of two colors among wavelength bands of red, green, and blue that differ from the wavelength band of the first light component;
  a first imaging element that includes a plurality of first pixels configured to receive the first light component separated by the optics and convert the first light component into electric signals; and
  a second imaging element that includes a plurality of second pixels arranged with a same arrangement and interval as the first pixels in the first imaging element, each of the plurality of second pixels occupying a substantially same area from a plan view perspective and each have a first color filter arranged thereon, each of the first color filters having a substantially same area,
  wherein the second imaging element includes (i) a plurality of first filters that are configured to transmit the light component of the wavelength band of one color in the light components of the wavelength bands of the two colors that are contained in the second light component, and (ii) a plurality of second filters that are white filters that are configured to transmit light components of a plurality of wavelength bands including at least the wavelength bands of red, green, and blue, each side of each of the plurality of first filters being adjacent to either only an edge of the second imaging element or only one of the white filters, and
  wherein the plurality of first filters and the plurality of second filters are arranged at sides of light receiving surfaces of the second pixels in accordance with the arrangement of the second pixels.

2. The medical imaging device according to claim 1, wherein at least one of the plurality of first filters and the plurality of second filters transmits light of a wavelength band of infrared rays.

3. The medical imaging device according to claim 1, wherein the first imaging element further includes a second color filter having a plurality of third filters that are configured to transmit the first light component are arranged at sides of light receiving surfaces of the first pixels in accordance with an arrangement of the first pixels.

4. The medical imaging device according to claim 1, wherein the optics separate the light from the outside by reflecting one of the incident first light component and the incident second light component only once and transmitting the other light component.

5. The medical imaging device according to claim 1, wherein
  the plurality of second filters are formed by a plurality of transmission filters configured to transmit light components of different wavelength bands, and
  the transmission filters include the white filter configured to transmit at least light components of the wavelength bands of red, green, and blue.

6. The medical imaging device according to claim 1, including only two imaging elements of the first imaging element and the second imaging element as imaging elements configured to image a subject to generate imaging signals.

7. A medical image acquisition system comprising:
  a medical imaging device including:
    optics that separate light from an outside into a first light component of a wavelength band of any one color among wavelength bands of red, green, and blue and a second light component containing light components of wavelength bands of two colors among wavelength bands of red, green, and blue that differ from the wavelength band of the first light component;
    a first imaging element that includes a plurality of first pixels configured to receive the first light component separated by the optics and convert the first light component into electric signals; and a second imaging element that includes a plurality of second pixels arranged with a same arrangement and interval as the first pixels in the first imaging element, each of the plurality of second pixels occupying a substantially same area from a plan view perspective and each have a first color filter arranged thereon, each of the first color filters having a substantially same area, wherein the second imaging element includes (i) a plurality of first filters that are configured to transmit the light component of the wavelength band of one color in the light components of the wavelength bands of the two colors that are contained in the second light component, and (ii) a plurality of second filters that are white filters that are configured to transmit light components of a plurality of wavelength bands including at least the wavelength bands of red, green, and blue, each side of each of the plurality of first filters being adjacent to either only an edge of the second imaging element or only one of the white filters, and wherein the plurality of first filters and the plurality of second filters are arranged at sides of light receiving surfaces of the second pixels in accordance with the arrangement of the second pixels; and an image processor that is electrically connected to the medical imaging device and configured to process received imaging signals to generate an image signal in accordance with the imaging signals.

8. An endoscope apparatus comprising a medical imaging device including:

optics that separate light from an outside into a first light component of a wavelength band of any one color among wavelength bands of red, green, and blue and a second light component containing light components of wavelength bands of two colors among wavelength bands of red, green, and blue that differ from the wavelength band of the first light component;

a first imaging element that includes a plurality of first pixels configured to receive the first light component separated by the optics and convert the first light component into electric signals; and a second imaging element that includes a plurality of second pixels arranged with a same arrangement and interval as the first pixels in the first imaging element, each of the plurality of second pixels occupying a substantially same area from a plan view perspective and each have a first color filter arranged thereon, each of the first color filters having a substantially same area, wherein the second imaging element includes (i) a plurality of first filters that are configured to transmit the light component of the wavelength band of one color in the light components of the wavelength bands of the two colors that are contained in the second light component, and (ii) a plurality of second filters that are white filters that are configured to transmit light components of a plurality of wavelength bands including at least the wavelength bands of red, green, and blue, each side of each of the plurality of first filters being adjacent to either only an edge of the second imaging element or only one of the white filters, and wherein the plurality of first filters and the plurality of second filters are arranged at sides of light receiving surfaces of the second pixels in accordance with the arrangement of the second pixels.

* * * * *